(12) United States Patent
Abreu et al.

(10) Patent No.: US 7,790,370 B2
(45) Date of Patent: Sep. 7, 2010

(54) MUTATIONS IN NOD2 ARE ASSOCIATED WITH FIBROSTENOSING DISEASE IN PATIENTS WITH CROHN'S DISEASE

(75) Inventors: Maria T. Abreu, New York, NY (US); Kent D. Taylor, Ventura, CA (US); Jerome I. Rotter, Los Angeles, CA (US); Huiying Yang, Cerritos, CA (US); Stephan R. Targan, Santa Monica, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 506 days.

(21) Appl. No.: 10/526,256

(22) PCT Filed: Jul. 30, 2003

(86) PCT No.: PCT/US03/23926

§ 371 (c)(1),
(2), (4) Date: May 5, 2006

(87) PCT Pub. No.: WO2004/020968

PCT Pub. Date: Mar. 11, 2004

(65) Prior Publication Data

US 2007/0072180 A1 Mar. 29, 2007

(51) Int. Cl.
*C07H 21/04* (2006.01)
*C12Q 1/68* (2006.01)
(52) U.S. Cl. .................. 435/6; 435/91.1; 435/91.2; 536/23.1; 536/24.3
(58) Field of Classification Search .................. None
See application file for complete search history.

(56) References Cited

U.S. PATENT DOCUMENTS

| | | | |
|---|---|---|---|
| 5,691,151 A | 11/1997 | Braun et al. | |
| 5,750,355 A | 5/1998 | Targan et al. | |
| 5,830,675 A | 11/1998 | Targan et al. | |
| 5,874,233 A | 2/1999 | Targan et al. | |
| 5,916,748 A | 6/1999 | Targan et al. | |
| 5,937,862 A | 8/1999 | Targan et al. | |
| 5,968,741 A | 10/1999 | Plevy et al. | |
| 6,074,835 A | 6/2000 | Braun et al. | |
| 7,138,237 B1 | 11/2006 | Targan et al. | |
| 2003/0092019 A1* | 5/2003 | Meyer et al. ............ | 435/6 |
| 2004/0053263 A1 | 3/2004 | Abreu et al. | |

OTHER PUBLICATIONS

Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Thisted (May 1998).*
Lakatos et al. (Orv. Hetil. vol. 145, No. 27, pp. 1403-1411, Jul. 2004).*
Kugathasan et al. (Gastroenterology, vol. 126, No. 4, Supp. 2, pp. A68, 524).*
Vavassori et al. (Inflamm Bowel Dis. vol. 10, No. 2, pp. 116-121, Mar. 2004).*
Ahmad et al. (Gastroenterology, vol. 122, pp. 854-866, Apr. 2002).*
Abreu et al (Gastroenterology, vol. 122, No. 4, Suppl. 1, ppA.29, 246).*
Radlmayr et al. (Gastroenterology, vol. 122, No. 7, pp. 2091-2095, Jun. 2002).*
Abreu et al. (Gastroenterology, vol. 123, pp. 679-688, Aug. 29, 2002).*
Radlmayr, M et al., (2002) "The c-insertion mutation of the NOD2 gene is associated with fistulizing and fibrostenotic phenotypes in crohn's disease", Gasteroenterology, pp. 2091-2902, vol. 122. No. 7.
Hampe, J. et al., (2002) "Association of NOD2 (CARD 15) genotype with clinical course of crohn's disease: a cohort study", The Lancet, Lancet Limited, pp. 1661-1665, vol. 359, No. 9318, London, GB.
Akolkar et al., "The IBD1 Locus for Susceptibility to Crohn's Disease Has a Greater Impact in Ashkenazi Jews with Early Onset Disease," *Am. J. Gastroenterol.* 96:1127-1132 (2001).
Annese et al., "Genetic analysis in Italian familiies with inflammatory bowel disease supports linkage to the *IBD1* locus—a GSIC study," *Eur. J. Hum. Genet.* 7:567-573 (1999).
Brant et al., "American Families with Crohn's Disease Have Strong Evidence for Linkage to Chromosome 16 but Not Chromosome 12," *Gastroenterology* 115:1056-1061 (1998).
Cavanaugh et al., "Analysis of Australian Crohn's disease pedigrees refines the localization for susceptibility to inflammatory bowel disease on chromosome 16," *Ann. Hum. Gent.* 62:291-298 (1998).
Cho et al., "Confirmation of a Susceptibility Locus for Crohn's Disease on Chromosome 16," *Inflamm. Bowel Dis.* 3:186-190 (1997).
Curran et al., "Genetic Analysis of Inflammatory Bowel Disease in a Large European Cohort Supports Linkage to Chromosomes 12 and 16," *Gastroenterology* 115:1066-1071 (1998).

(Continued)

*Primary Examiner*—Jeanine A Goldberg
(74) *Attorney, Agent, or Firm*—Townsend and Townsend and Crew LLP

(57) ABSTRACT

The present invention provides a method of diagnosing or predicting susceptibility to a clinical subtype of Crohn's disease characterized by fibrostenosing disease by determining the presence or absence in an individual of a fibrostenosis-predisposing allele linked to a NOD2/CARD15 locus, where the presence of the fibrostenosis-predisposing allele is diagnostic of or predictive of susceptibility to the clinical subtype of Crohn's disease characterized by fibrostenosing disease. In a method of the invention, the clinical subtype of Crohn's disease can be, for example, characterized by fibrostenosing disease independent of small bowel involvement. The invention also provides a method of optimizing therapy in an individual by determining the presence or absence in the individual of a fibrostenosis-predisposing allele linked to a NOD2/CARD15 locus, diagnosing individuals in which the fibrostenosis-predisposing allele is present as having a fibrostenosing subtype of Crohn's disease, and treating the individual having a fibrostenosing subtype of Crohn's disease based on the diagnosis.

15 Claims, 15 Drawing Sheets

OTHER PUBLICATIONS

Gasche et al., "A Simple Classification of Crohn's Disease: Report of the Working Party for the World Congresses of Gastroenterology, Vienna 1998," *Inflammatory Bowel Disease* 6:8-15 (2000).

Greenstein et al., "Perforating and non-perforating indications for repeated operations in Crohn's disease: evidence for two clinical forms," *Gut* 29:588-592 (1988).

Hampe et al., "A Genomewide Analysis Provides Evidence for Novel Linkages in Inflammatory Disease in a Large European Cohort," *Am. J. Hum. Genet.* 64:808-816 (1999).

Hampe et al., "Association between insertion mutation in *NOD2* gene and Crohn's disease in German and British populations," *Lancet* 357:1925-1928 (2001).

Hugot et al., "Mapping of a susceptibility locus for Crohn's Disease on chromosome 16," *Nature* 379:821-823 (1996).

Hugot et al., "Association of NOD2 leucine-rich repeat variants with susceptibility to Crohn's disease," *Nature* 411:599-603 (2001).

Inohara et al., "Human Nod1 Confers Responsiveness to Bacterial Lipopolysaccharides," *J. Biol. Chem.* 276:2551-2554 (2001).

Kutyavin et al., "Oligonucleotides with conjugated dihydropyrroloindole tripeptides: base composition and backbone effects on hybridization," *Nucleic Acid Res.* 25:3718-3723 (1997).

Kutyavin et al., "3'-Minor groove binder-DNA probes increase sequence specificity at PCR extension temperatures," *Nuc. Acids Research* 28:655-661 (2000).

Lesage et al., "*CARD15/NOD2* Mutational Analysis and Genotype-Phenotype Correlation in 612 Patients with Inflammatory Bowel Disease," *Am. J. Hum. Genet.* 70:845-857 (2002).

Livak, "Allelic discrimination using fluorogenic probes and the 5' nuclease assay," *Genetic Analysis* 14:143-149 (1999).

Murillo et al., "*CARD15* gene and the classification of Crohn's disease," *Immunogenetics* 54:59-61 (2002).

Ogura et al., "A frameshift mutation in *NOD2* associated with susceptibility to Crohn's Disease," *Nature* 411:603-606 (2001).

Ogura et al., "Nod2, a Nod1/Apaf-1 Family Member That Is Restricted to Monocytes and Activates NF-kB," *J. Biol. Chem.* 276:4812-4818 (2001).

Ohmen et al., "Susceptibility locus for inflammatory bowel disease on chromosome 16 has a role in Crohn's disease but not in ulcerative colitis," *Hum. Mol. Genet.* 5:1679-1683 (1996).

Parkes et al., "Susceptibility loci in inflammatory bowel disease," *Lancet* 348:1588 (1996).

Vasiliauskas et al., "Perinuclear Antineutrophil Cytoplasmic Antibodies in Patients with Crohn's Disease Define a Clinical Subgroup," *Gastroenterology* 110:1810-1819 (1996).

Vasiliauskas et al., "Marker antibody expression stratifies Crohn's disease into immunologically homogenous subgroups with distinct clinical characteristics," *Gut* 47;487-496 (2000).

Vermeire et al., "*CARD15* Genetic Variation in a Quebec Population: Prevalence, Genotype-Phenotype Relationship, and Haplotype Structure," *Am. J. Hum. Genet.* 71:74-83 (2002).

GenBank Accession No. AC007728.

GenBank Accession No. NM_022162.

NCBI SNP ID No. rs2066844.

NCBI SNP ID No. rs2066845.

NCBI SNP ID No. rs2066847.

* cited by examiner

FIGURE 5

SNP 8

```
5' ACCTTCAGAT CACAGCAGCC TTCCTCCCAG GCCTCTTGTC CCGCCACCAC    50
3' TGGAAGTCTA GTGTCGTCGG AAGGAGGGTC CGGAGAACAG GGCGGTGGTG

TGGGGCCTGC TGGCTGCGTG CCAGACATCT GCAAGCCCC  GGCTCCTGCG    100
   ACCCCGGACG ACCGACGCAC GGTCTGTAGA CGTTCGGGG  CCGAGGACGC

CGGCCTGTC CCGGCCTGGT GTCTGCCCCG CAGCCTCCGC AAGCACTTCC    150
   GCCGGACAG GGCCGGACCA CAGACGGGGC GTCGGAGGCG TTCGTGAAGG

ACTCCATCCC GCCACTCCA CCGGGTGAGG CCAACAGCGT GCATCCCATG     200
   TGAGGTAGGG CGGTGAGGT GGCCCACTCC GGTTCTCGCA CGTAGGGTAC

CCCGCGTTCA TCTGCCTCAT CGGACCCTG TACGAGATCC ACGAGGACGC      250
   GGGCGCAAGT AGACCGAGTA GCCCTGGGAC ATGCTCTAGG TGCTCCTGCG

GCTCCCTCGG AAGCCTCCAC GTCCCCTGAA TGTTCGGCAC CTCAAGTTCA    300
   CGAGGGAGCC TTCGGAGGTG CACGGGACTT ACAAGCCGTG GAGTTCAAGT

CATTTGCAG TGTGCCCCC ACTGAGTGTG CTCCCCTCGC CTTTCTGCTG      350
   GTAAAACGTC ACACCGGGGG TGACTCACAC GAGGGGACGG GAAACACGAC

CAGCACCTCC GCGGCGCCGT GCCCCTGCAG CTCCACTCCA ACTCTGTGGG    400
   GTCGTGGAGG CCGCCGCCGA CGGGGACGTC GAGGTGAGGT TGAGACACCC

TGACATTCCC GTGCAGCGGC TCCTGCCTTG CCTTGGTGTC TGCAAGGCTC    450
   ACTGTAAGGG CACGTCGCCG AGGACGGAAC GGAACCACAG ACGTTCCGAG

TGTAGTGAGT GTTACTGGGC ATTCCTGTTC AGTATGGGG CACC 3'        494
   ACATCACTCA CAATGACCCG TAAGGACAAG TCATACCCC GTGG 5'
```

SEQ ID NO 1
SEQ ID NO 2

Figure 6

SNP 12

```
5'ATCAAAACCC TGAGAGGACA AGGGACATTT CCAAGTCACC CAGAAAGACT   50
3'TAGTTTTGGG ACTCTCCTGT TCCCTGTAAA GGTTCAGTGG GTCTTTCTGA

CGAGTGTCCT CTCTTCAAAT CCAATGGTCT TTTTTCCTTA CTCCATTGCC  100
  GCTCACAGGA GAGAAGTTTA GGTTACCAGA AAAAGGAAT  GAGGTAACGG

TAACATTGTG GGGTAGAAAT AAAGTTCAAA GACCTTCAGA ACTGGCCCCA  150
  ATTGTAACAC CCCATCTTTA TTTCAAGTTT CTGGAAGTCT TGACCGGGT

GCTCCTCCCT CTTCACCTGA TCTCCCCAAG AAAACTGCAG GATAGACTCT  200
  CGAGGAGGGA GAAGTGGACT AGAGGGGTTC TTTTGACGTC CTATCTGAGA

GAAGCTTACC TGACCACCT  CAAGCTCTGG TGATCACCCA AGGCTTCAGC  250
  CTTCGAATGG ACTGGTGGA  GTTCGAGACC ACTAGTGGGT TCCGAAGTCG

CAGGGCCTGG GCCCCCTCGT CACCCActct gttgcccag aaTCTGAAAA  300
  GTCCCGGACC CGGGGGAGCA GTGGGTgaga caacggggtc ttAGACTTTT GGCCAAAAGA GTCAACAGAC AGTGTCAGTG AGTACCTGAT ATGTGTTCTA  350
  CCGGTTTTCT CAGTTGTCTG TCACAGTCAC TCATGGACTA TACACAAGAT GACATGAACT AACAGTCCTC CTCCCTCTGC AGTCCCAGCC AGAGGGCCAG  400
  CTGTACTTGA TTGTCAGGAG GAGGGAGACG TCAGGGTCGG TCTCCCCGTC GACCACTCAA TCCCAGAGTG GCCTCACTGG GCCTCCTGGT CCCAGCAAAG  450
  CTGGTGAGTT AGGGTCTCAC CGGAGTGACC CGGAGGACCA GGGTCGTTTC TGGACCTGCC TCCATCTTTT GGGTGGCATC GCCAAACTTA ACCAAGAGT   500
  ACCTGGACGG AGGTAGAAAA CCCACCGTAC CGGTTTGAAT TGGGTTCTCA TTTCAGTCGC TTTACATTAC AGACTTAGAG AATAGTACAG3'-SEQ ID NO 3 540
  AAAGTCACCG AAATGTAATG TCTGAATCTC TTATCATCTC5'-SEQ ID NO 4
```

FIGURE 7

SNP 13

```
5'TTTAAAAATG AAATCATTGC TCCCTACTTA AAGAGGTAAA GACTTCTTTC   50
3'AAATTTTTAC TTTAGTAACG AGGGATGAAT TTCTCCATTT CTGAAGAAAG

TTACACAGAG AATCAGATCC TTCACATGCA GAATCATTCT CACTGAATGT  100
  AATCTGTCTC TTAGTCTAGG AAGTGTACGT CTTAGTAAGA GTGACTTACA

CAGAATCAGA AGGGATCCTC AAAATTCTGC CATTCCTCTC TCCGGTCACC  150
  GTCTTAGTCT TCCCTAGGAG TTTTAAGACG GTAAGGAGAG AGGCCAGTGG

CCATTTTACA GATAGAAAAA CTGAGGTTCG GAGAGCTAAA ACAGGCCTGC  200
  GGTAAAATGT CTATCTTTTT GACTCCAAGC CTCTCGATTT TGTCCGGACG

CCAGGGCCT  TACCAGACTT  CCAGGATGG  GTCATT cctt  tcaaggggcc  250
  GGTCCCGGA  ATGGTCTGAA  GGTCCTACCA  CAGTAA ggaa  agttcccgg tgc AGGAGGG CTTCTGCCCC TAGGTAGGTG ATGCAGTTAT TGGACAACCT  300
  acg TCCTCCC GAAGACGGGG ATCCATCCAC TACGTCAATA ACCTGTTGGA GGAAAAGAAG ATACAATGGT GAGCTTCAAG GATTCTTGGT TTTCCTCTTG  350
  CCTTTTCTTC TATGTTACCA CTCGAAGTTC CTAAGAACCA AAAGGAGAAC AAACTGTCCA GTTAAAGAGA CTGCAGGAGT TAGCCAGTCT ACTGAAGCCC  400
  TTTGACAGGT CAATTTCTCT GACGTCCTCA ATCGGTCAGA TGACTTCGGG ACCTGTCCCT TAGACACATC CTGCTCATGT CTGAGATTCC CAATGAGCTC  450
  TGGACAGGGA ATCTGTGTAG GACGAGTACA GACTCTAAGG GTTACTCGAG ATCAACAAAG GCTCAGTACC ATCAGTGAAA TGTAACGGTC TCTCTTCCAT  500
  TAGTTGTTTC CGAGTCATGG TAGTCACTTT ACATTGCCAG AGAGAAGGTA TCACTAGATG AGTTTATCAA ATTAAGTAGG CACTCCCTTA G 3'-SEQ ID NO 5  541
  AGTGATCTAC TCAAATAGTT TAATTCATCC GTGAGGGAAT C 5'-SEQ ID NO 6
```

FIGURE 8

SNP 5

```
5' AACAGCAGTG CTCAAACAGT AGAGTCCGCA CAGAGAGTGG TTTGGCCATG    50
3' TTGTCGTCAC GAGTTTGTCA TCTCAGGCGT GTCTCTCACC AAACCGGTAC

CACTGCAGCT GCCGGCAGCT GAATGCGAAG ACAAAGAGAA ATTCCTGGAA   100
   GTGACGTCGA CGGCCGTCGA CTTACGCTTC TGTTTCTCTT TAAGGACCTT

GTCTTGCCCT GCAGCCCACA CCAAGTCCAG CCGCTGCAGG ACGGTCCTCT   150
   CAGAACGGGA CGTCGGGTGT GGTTCAGGTC GGCGACGTCC TGCCAGGAGA

TGCCACTGCC CGCCTCACCC ACCACCAGCA CAGTGTCCGC ATCGTCATTG   200
   ACGGTGACGG GCGGAGTGGG TGGTGGTCGT GTCACAGGCG TAGCAGTAAC

AGGTGGCCAG CGGTCCTCAA CAGCTCCTCC AGCCCAGGG TGCCTGGGCT    250
   TCCACCGGTC GCCAGGAGTT GTCGAGGAGG TCGGGTCCC ACGGACCCGA

CTTCGCCGGg ggtccagcca tgTCCACATC TGCCCAGACC TCCAGGACAT   300
   GAAGCGGCCc ccaggtcggt acAGGGTGTAG ACGGGTCTGG AGGTCCTGTA TCTCTGTGTA TATGTCCTCC AGGCAGACCG TCTCTGCTCC ATCATAGGTA   350
   AGAGACACAT ATACAGGAGG TCCGTCTGGC AGAGACGAGG TAGTATCCAT CTGAGGAAGC GAGACTGAGC AGACACCGTG GTCCTCAGCT TGGCCATATA   400
   GACTCCTTCG CTCTGACTCG TCTGTGGCAC CAGGAGTCGA ACCGGTATAT CTTCTTCCAT GTGCCAGCTG GAAGGCAGAA GAAGAGGCAG ATGAAGGTGG   450
   GAAGAAGGTA CACGGTCGAC CTTCCGTCTT CTTCTCCGTC TACTTCCACC CACCATGGTG AAGAGCGGAC CTAACCAGAC AATGGGCTCC TGGGGGGAC    500
   GTGGTACCAC TTCTCGCCTG GATTGGTCTG TTACCCGAGG ACCCCCCTG GCTGACATAA CTGAAGGGAT AGGAGAGCCA GCGGGCGCCC3'-SEQ ID NO 7 540
   CGACTGTATT GACTTCCCTA TCCTCTCGGT CGCCCGCGGG5'-SEQ ID NO 8
```

```
5' CCACTGGGCA CCCACTACCA ATGGATTGGA ATTGGTCCTT AAGATAAAAT    50
3' GGTGACCCGT GGGTGATGGT TACCTAACCT TAACCAGGAA TTCTATTTTA

GTACCTGATC CACCCCAATA TCTTCAATTT ACAGATACTG TATCAAAACC   100
   CATGGACTAG GTGGGGTTAT AGAAGTTAAA TGTCTATGAC ATAGTTTTGG

CTGAGAGGAC AAGGGACATT TCCAAGTAC CCAGAaagac tcgagtgtcc   150
   GACTCTCCTG TTCCCTGTAA AGGTTCAGTG GGTCTttctg agctcacagg tCTCTTGAAA TCCAATGGTC TTTTTTCCTT ACTCCATTGC CTAACATTGT   200
   aGAGAACTTT AGGTTACCAG AAAAAAGGAA TGAGGTAACG GATTGTAACA GGGGTAGAAA TAAAGTTCAA AGACCTTCAG AACTGGCCCC AGCTCCTCCC   250
   CCCCATCTTT ATTTCAAGTT TCTGGAAGTC TTGACCGGGG TCGAGGAGGG TCTTCACCTG ATCTCCCCAA GAAAACTGCA GGATAGACTC TGAAGCTTAC   300
   AGAAGTGGAC TAGAGGGGTT CTTTTGACGT CCTATCTGAG ACTTCGAATG CTGAGCCACC TCAAGCTCTG GTGATCACCC AAGGCTTCAG CCAGGGCCTG   350
   GACTCGGTGG AGTTCGAGAC CACTAGTGGG TTCCGAAGTC GGTCCCGGAC GGCCCCCTCG TCACCCACTC TGTTGCCCCA GAATCTGAAA AGGCCAAAAG   400
   CCGGGGGAGC AGTGGGTGAG ACAACGGGGT CTTAGACTTT TCCGGTTTTC AGTCAACAGA CAGTGTCAGT GAGTACCTGA TATGTGTTCT AGACATGAAC   450
   TCAGTTGTCT GTCACAGTCA CTCATGGACT ATACACAAGA TCTGTACTTG TAACAGTCCT CCTCCCTCTG CAGTCCCACC CAGAGGGGCA GGACCACTCA   500
   ATTGTCAGGA GGAGGGAGAC GTCAGGGTGG GTCTCCCGT CCTGGTGAGT ATCCCAGAGT GGGCTCACTG 3'-SEQ ID NO 9                     520
   TAGGGTCTCA CCCGAGTGAC 5'-SEQ ID NO 10
```

MUTATIONS IN NOD2 ARE ASSOCIATED WITH FIBROSTENOSING DISEASE IN PATIENTS WITH CROHN'S DISEASE

ACKNOWLEDGMENT

This work was supported by grant DK46763 and DK54967 awarded by NIDDK. The United States government has certain rights in this invention.

BACKGROUND OF THE INVENTION

1. Field of the Invention

The invention relates generally to the fields of genetics and autoimmune disease and, more specifically, to mutations linked to the NOD2/CARD15 gene and genetic methods for diagnosing clinical subtypes of Crohn's disease.

2. Background Information

Inflammatory bowel disease (IBD) is the collective term used to describe two gastrointestinal disorders of unknown etiology: Crohn's disease (CD) and ulcerative colitis (UC). The course and prognosis of IBD, which occurs world-wide and is reported to afflict as many as two million people, varies widely. Onset of IBD is predominantly in young adulthood with diarrhea, abdominal pain, and fever the three most common presenting symptoms. The diarrhea may range from mild to severe, and anemia and weight loss are additional common signs of IBD. Of all patients with IBD, ten percent to fifteen percent will require surgery over a ten year period. In addition, patients with IBD are at increased risk for the development of intestinal cancer. Reports of an increasing occurrence of psychological problems, including anxiety and depression, are perhaps not surprising symptoms of what is often a debilitating disease that strikes people in the prime of life.

Crohn's disease is a classification representing a number of heterogeneous disease subtypes that affect the gastrointestinal tract and produce similar symptoms. Both environmental and genetic factors likely contribute to the etiology of such disease subtypes. Patients with Crohn's disease can be classified, for example, into subtypes based on the presence of fibrostenosing disease, internal-perforating disease, perianal fistulizing disease or ulcerative colitis-like disease according to previously described criteria. The fibrostenosing disease subtype is characterized by documented persistent intestinal obstruction or intestinal resection for intestinal obstruction. The extensive and often protracted clinical testing required to diagnose Crohn's disease and disease subtypes may delay optimal treatment and involves invasive procedures such as endoscopy.

Identification of genetic markers which are closely associated with a clinical subtype of Crohn's disease would provide the basis for novel genetic tests and eliminate or reduce the need for the battery of laboratory, radiological, and endoscopic evaluations typically required to determine disease subtype. The availability of methods for diagnosing clinical subtypes of Crohn's disease would represent a major clinical advance that would aid in the therapeutic management of Crohn's disease and would further lay the groundwork for the design of treatment modalities which are specific to a particular disease subtype. Such methods can reduce costs associated with treatment of unresponsive disease subtypes and eliminate the disappointment of those needlessly undergoing ineffective therapy. In particular, a reliable genetic test for the fibrostenosing subtype of Crohn's disease would be highly prized as a non-invasive method for the early diagnosis of this disease subtype and would also be useful for predicting susceptibility to the fibrostenosing subtype of Crohn's disease in asymptomatic individuals, making prophylactic therapy possible. The present invention satisfies this need and provides related advantages as well.

SUMMARY OF THE INVENTION

The present invention provides a method of diagnosing or predicting susceptibility to a clinical subtype of Crohn's disease characterized by fibrostenosing disease by determining the presence or absence in an individual of a fibrostenosis-predisposing allele linked to a NOD2/CARD15 locus, where the presence of the fibrostenosis-predisposing allele is diagnostic of or predictive of susceptibility to the clinical subtype of Crohn's disease characterized by fibrostenosing disease. In a method of the invention, the clinical subtype of Crohn's disease can be, for example, characterized by fibrostenosing disease independent of small bowel involvement.

The invention also provides a method of optimizing therapy in an individual by determining the presence or absence in the individual of a fibrostenosis-predisposing allele linked to a NOD2/CARD15 locus, diagnosing individuals in which the fibrostenosis-predisposing allele is present as having a fibrostenosing subtype of Crohn's disease, and treating the individual having a fibrostenosing subtype of Crohn's disease based on the diagnosis.

Figure 1:
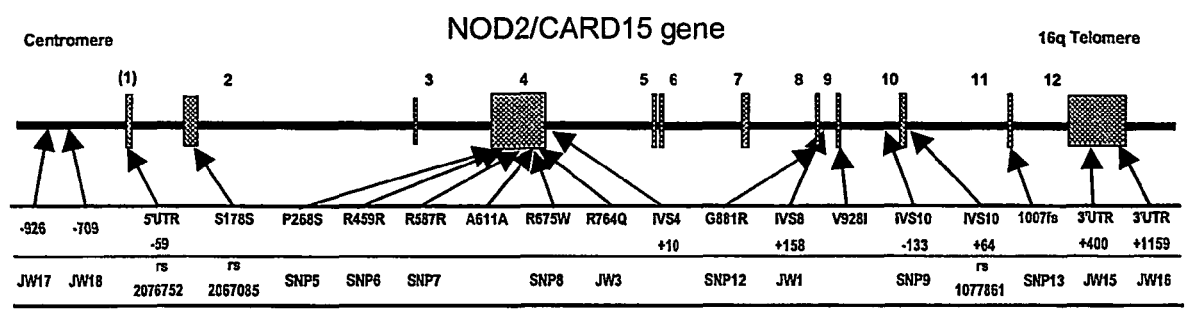
FIG. 1 shows the NOD2/CARD15 locus intron and exon structure with the location of SNP 8, SNP 12, SNP 13, and JW1 as well as other markers.

Patients were separated by the presence of fibrostenosing disease with perforating complications ("Fib+perf") or fibrostenosing disease without perforating complications ("Fib only") compared with patients with perforating complications and without evidence of fibrostenosis ("Perf only").

FIG. 5 shows the nucleotide sequence of NOD2/CARD15 surrounding SNP 8. The top strand is labeled as SEQ ID NO:1 and the bottom strand is labeled as SEQ ID NO:2. Nucleotide sequences which can be used as primers for PCR amplification are indicated. In addition, the position of a nucleotide sequence which can be used as a probe in an allelic discrimination assay is indicated, in this figure, by a box and lowercase letters. The underlined nucleotide indicates the position of the polymorphic site.

FIG. 6 shows the nucleotide sequence of NOD2/CARD15 surrounding SNP 12. The top strand is labeled as SEQ ID NO:3 and the bottom strand is labeled as SEQ ID NO:4. Nucleotide sequences which can be used as primers for PCR amplification are indicated. In addition, the position of a nucleotide sequence which can be used as a probe in an allelic discrimination assay is indicated, in this figure, by a box and lower case letters. The underlined nucleotide indicates the position of the polymorphic site.

FIG. 7 shows the nucleotide sequence of NOD2/CARD15 surrounding SNP 13. The top strand is labeled as SEQ ID NO:5 and the bottom strand is labeled as SEQ ID NO:6. Nucleotide sequences which can be used as primers for PCR amplification are indicated. In addition, the position of a nucleotide sequence which can be used as a probe in an allelic discrimination assay is indicated, in this figure, by a box and lower case letters. The underlined nucleotide indicates the position of the polymorphic site.

FIG. 8 shows the nucleotide sequence of NOD2/CARD15 surrounding SNP 5. The top strand is labeled as SEQ ID NO:7 and the bottom strand is labeled as SEQ ID NO:8. Nucleotide sequences which can be used as primers for PCR amplification are indicated. In addition, the position of a nucleotide sequence which can be used as a probe in an allelic discrimination assay is indicated, in this figure, by a box and lower case letters. The underlined nucleotide indicates the position of the polymorphic site.

FIG. 9 shows the nucleotide sequence of NOD2/CARD15 surrounding the JW1 variant sequence. The top strand is labeled as SEQ ID NO:9 and the bottom strand is labeled as SEQ ID NO:10. Nucleotide sequences which can be used as primers for PCR amplification are indicated. In addition, the position of a nucleotide sequence which can be used as a probe in an allelic discrimination assay is indicated, in this figure, by a box and lower case letters. The underlined nucleotide indicates the position of the polymorphic site.

Figure 10:
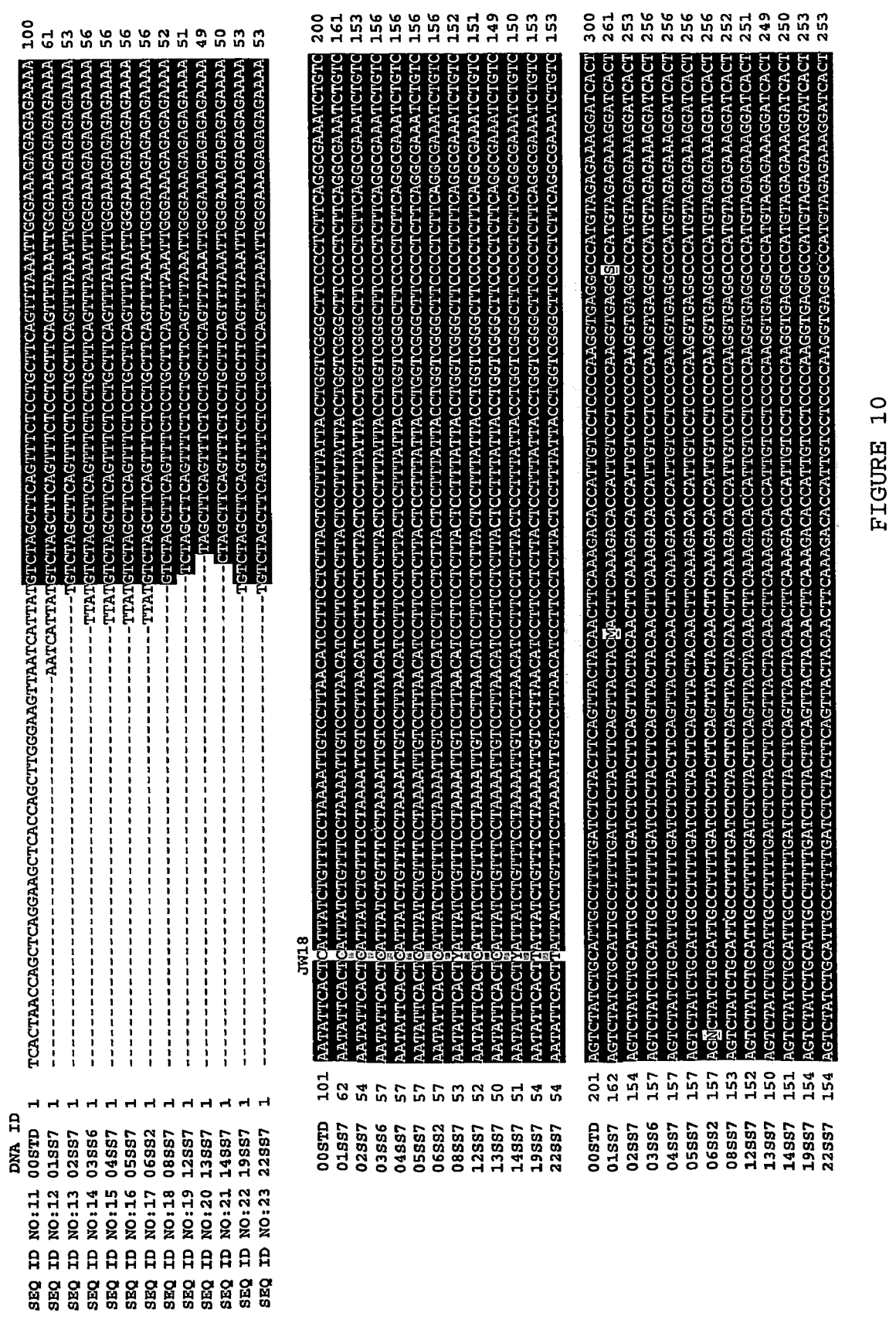
Figure 10:
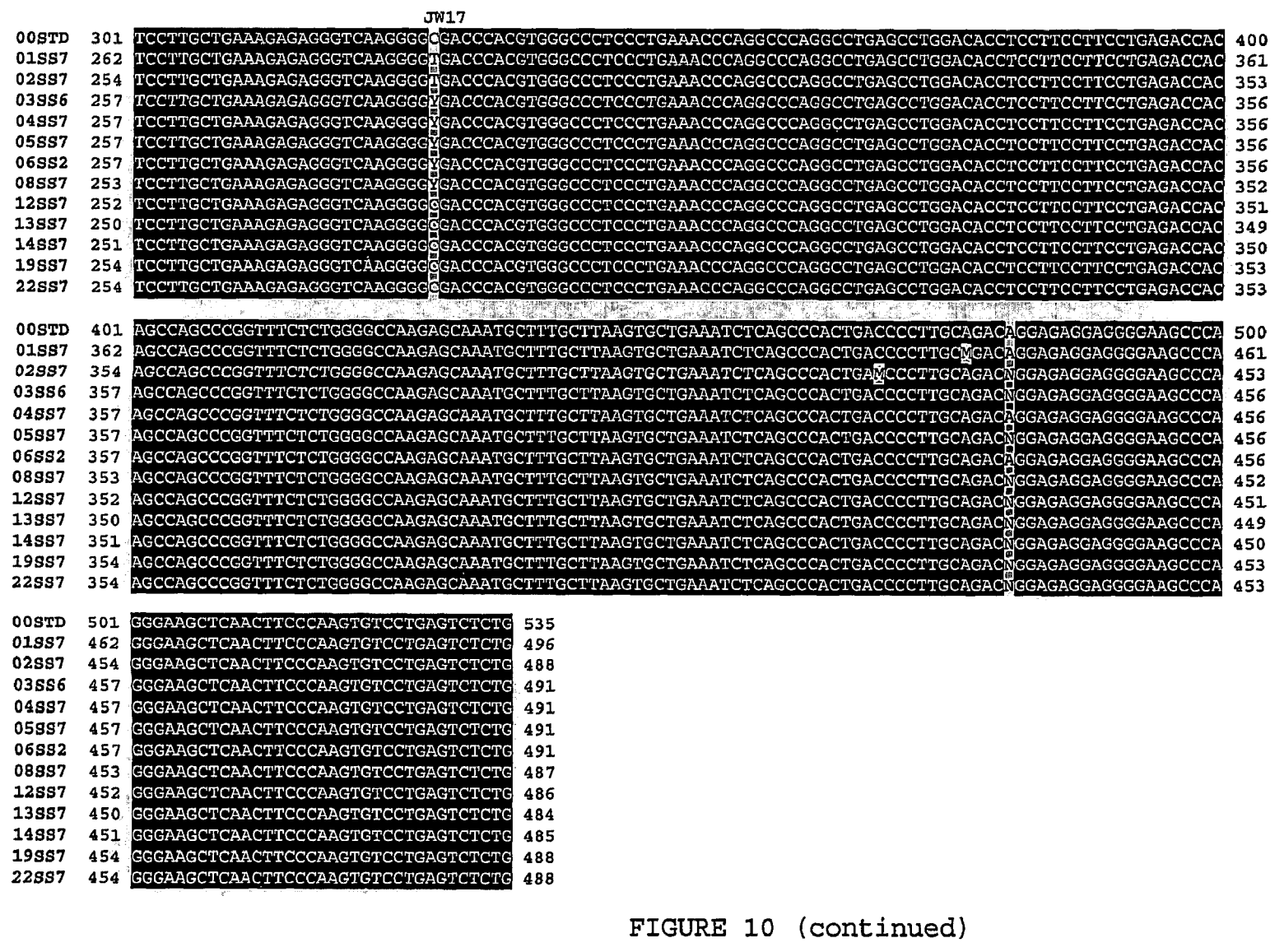

FIG. 10 shows the nucleotide sequence of the 5' untranslated region of NOD2/CARD15 in 12 individuals (SEQ ID NOS:12-23) compared to the wild-type NOD2/CARD15 sequence (SEQ ID NO:11). Areas of sequence identity are shaded. The location of two polymorphic sites, JW18 and JW17, are indicated.

Figure 11A:
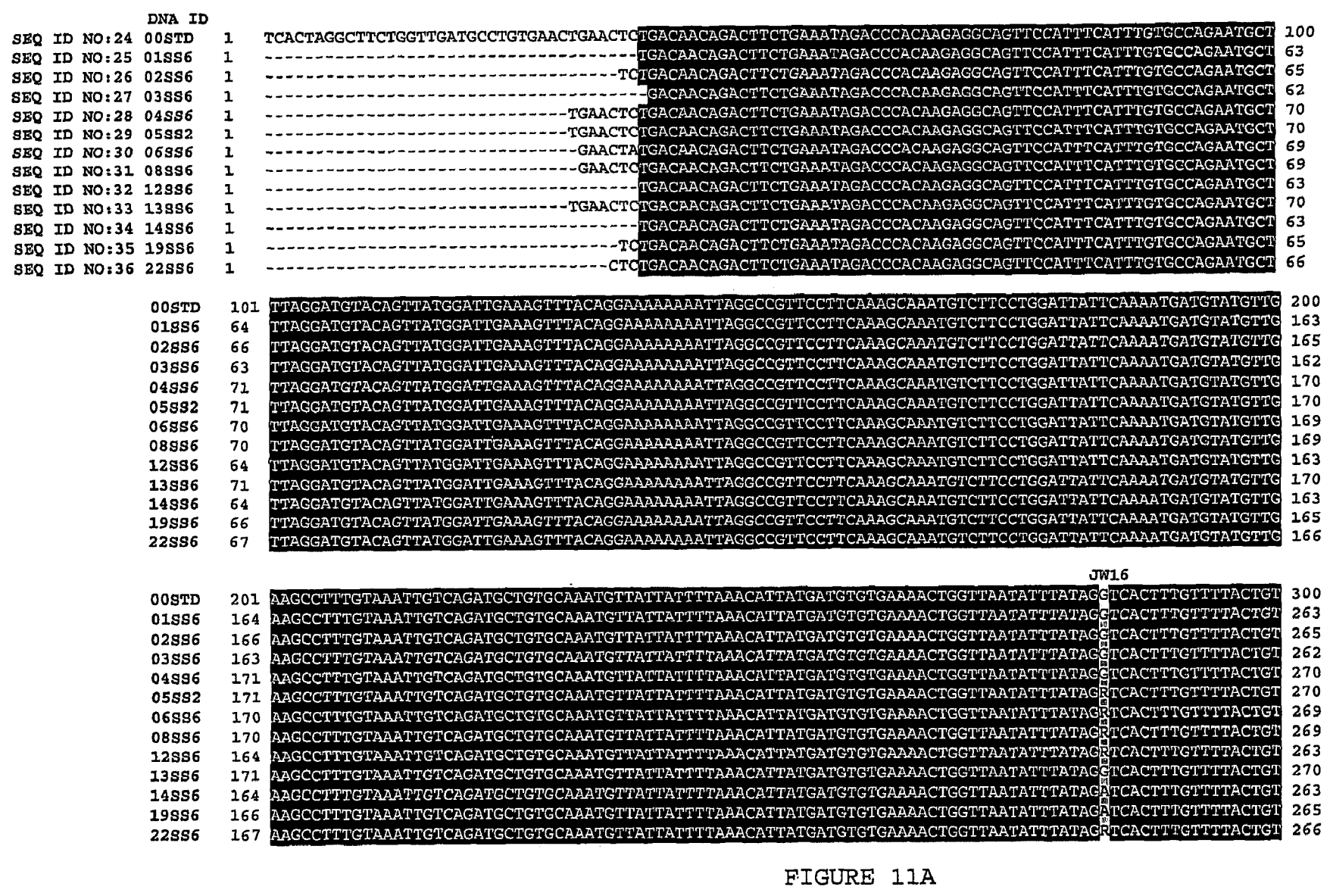
Figure 11A:
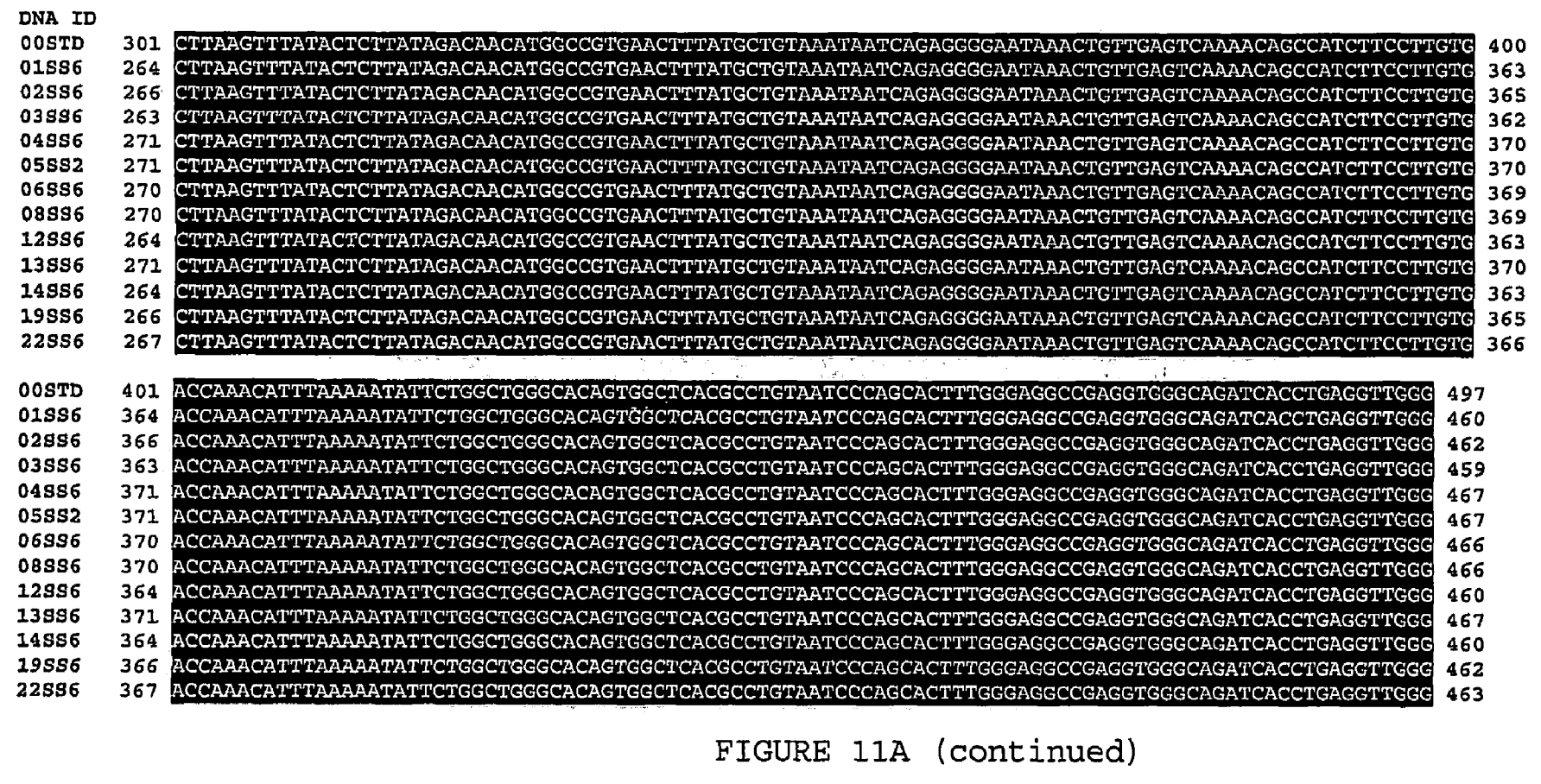
Figure 11B:
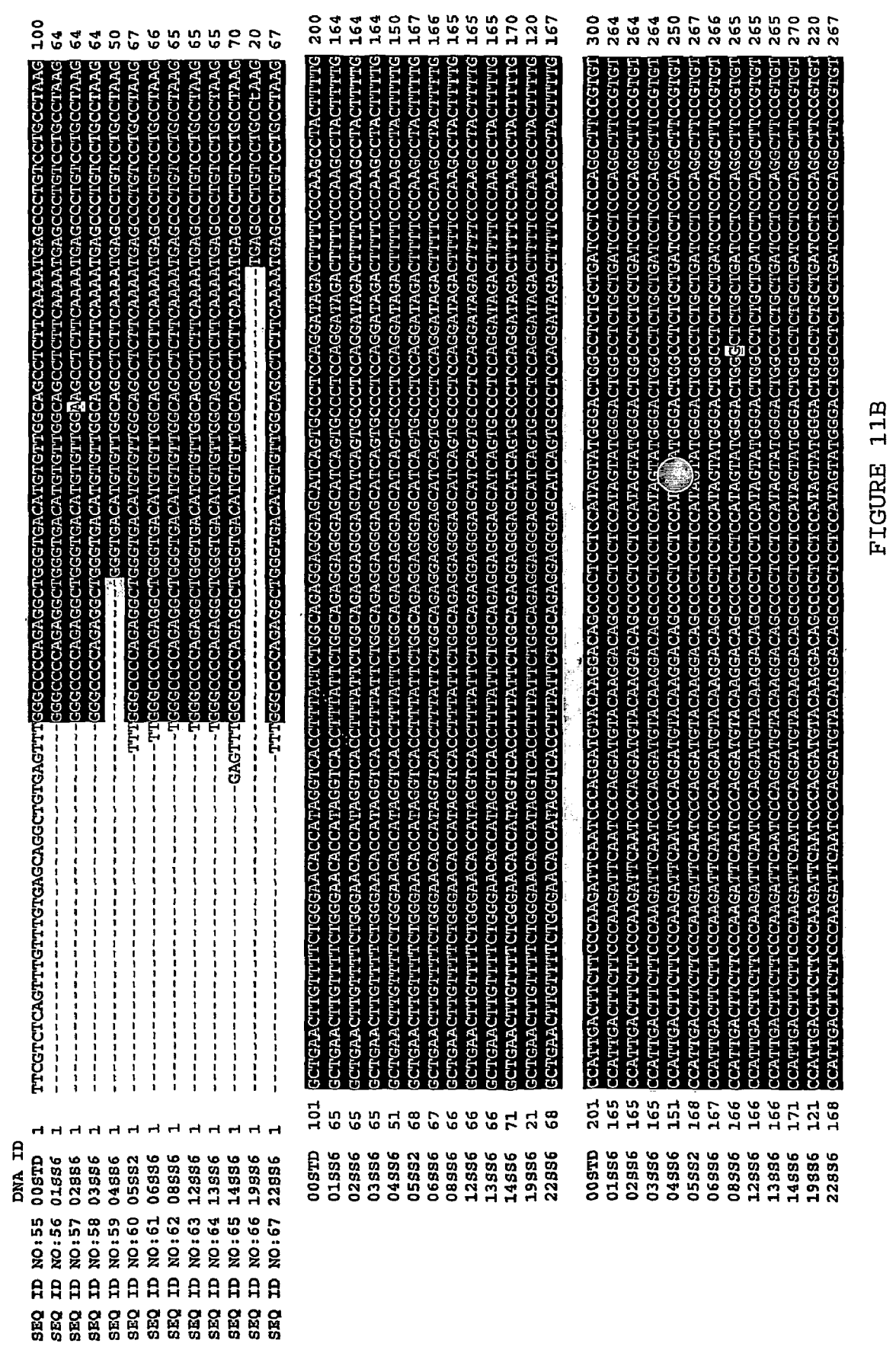
Figure 11B:
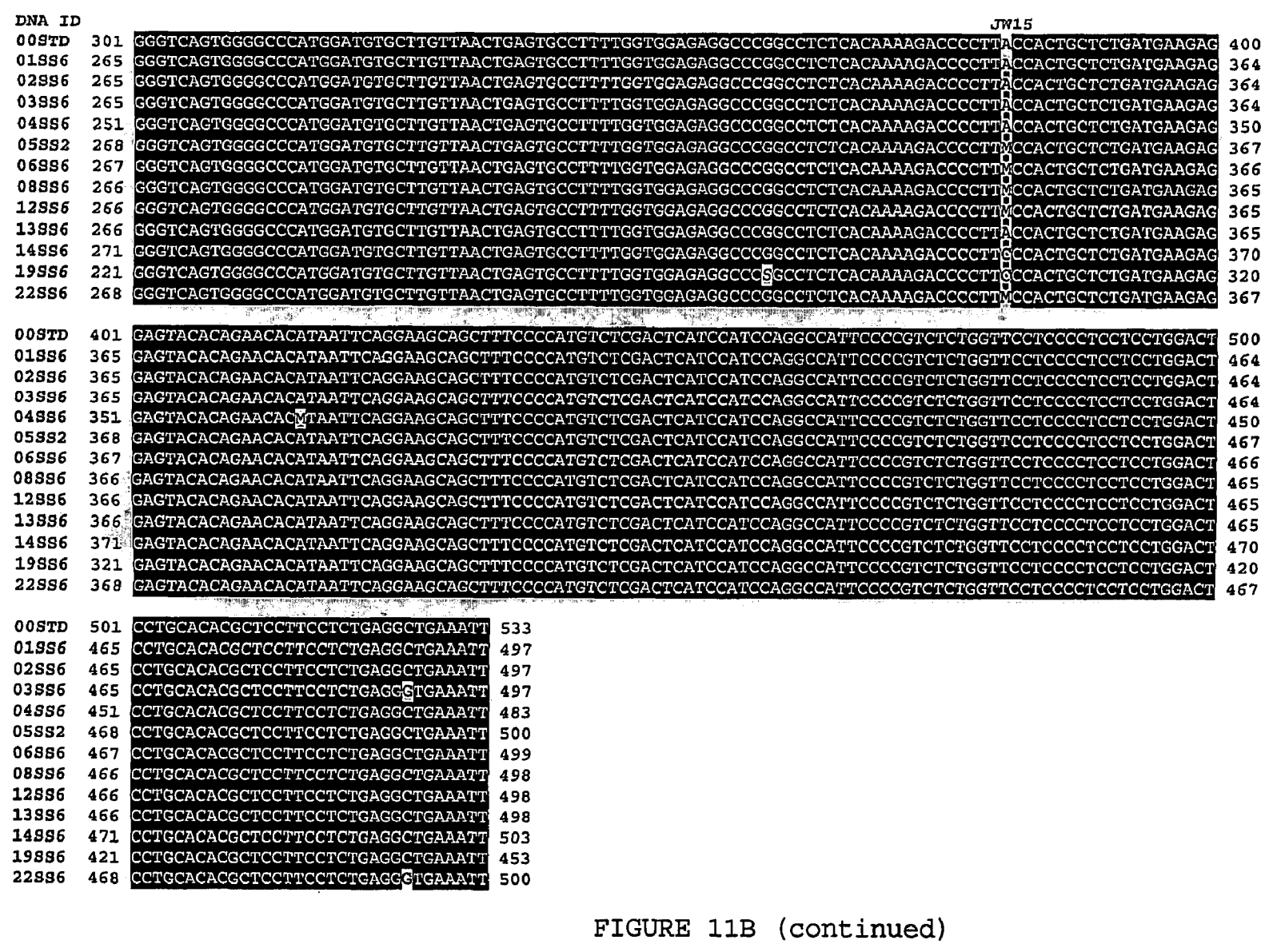

FIG. 11 shows the nucleotide sequence of the 3' untranslated region of NOD2/CARD15 in 12 individuals. Areas of sequence identity are shaded. The location of two polymorphic sites, JW15 and JW16, are indicated. FIG. 11 A shows the nucleotide sequence of the 3' untranslated region of NOD2/CARD15 in 12 individuals (SEQ ID NOS:25-36) compared to the wild-type NOD2/CARD15 sequence (SEQ ID NO:24) and the location of JW16. FIG. 11 B shows the nucleotide sequence of the 3' untranslated region of NOD2/CARD15 in 12 individuals (SEQ ID NOS:56-67) compared to the wild-type NOD2/CARD15 sequence (SEQ ID NO:55) and the location of JW15.

DETAILED DESCRIPTION OF THE INVENTION

The present invention is directed to the exciting discovery of disease-predisposing alleles that are closely associated with the fibrostenosing disease subtype of Crohn's disease. These fibrostenosis-predisposing alleles are linked to a NOD2/CARD15 locus as described further below and can be used to diagnose or predict susceptibility to the fibrostenosing disease subtype of Crohn's disease.

As disclosed herein, genotyping and other clinical characterization approaches were used to identify a strong association between disease-predisposing alleles and the fibrostenosing disease subtype of Crohn's disease. In particular, two cohorts of Crohn's disease patients were assembled and clinically characterized (see Example I and Table 1). These patients were also genotyped for three single nucleotide polymorphisms (SNPs) in the NOD2/CARD15 gene, SNP 8, SNP 12, and SNP 13, which are polymorphic markers associated with Crohn's disease. As disclosed herein, univariate analysis indicated that a "2" allele at SNP 8, SNP 12, or SNP 13 of the NOD2/CARD15 locus was significantly associated with fibrostenosing disease in Cohort 1 ($p=0.049$, see Table 5). In addition, a positive association at a less stringent significance level was also observed with small bowel involvement and younger age of onset, and a negative association was observed with ulcerative colitis-like disease in this cohort. With respect to serologic markers, patients with the "2" allele at SNP 13 were more likely to express anti-*Saccharomyces cerevisiae* antibodies (ASCA) ($p=0.053$).

The results obtained with Cohort 1 were further tested using Cohort 2 as disclosed herein in Example IV. As with Cohort 1, Cohort 2 demonstrated a significant association between a "2" allele at SNP 8, SNP 12, or SNP 13 of the NOD2/CARD15 locus and fibrostenosing disease ($p=0.002$, see Table 6). Furthermore, the significance between a "12" allele at SNP 8, SNP 12, or SNP 13 of the NOD2/CARD15 locus and fibrostenosing disease increased when the two cohorts were analyzed together ($p=0.001$, see FIG. 2).

As further disclosed herein in Example V, a "2" allele at SNP 8, SNP 12, or SNP 13 of the NOD2/CARD15 locus was associated with fibrostenosing disease in both Jewish and non-Jewish individuals. Approximately 46% of Crohn's disease patients with fibrostenosing disease (Jewish individuals 52% vs. non-Jewish individuals 42%) had at least one of these rare variant alleles compared with only 23% (Jewish individuals 21.6% vs. non-Jewish individuals 25%) of Crohn's disease patients without fibrostenosing disease (Odds ratio, 2.8; 95% Confidence interval, 1.56-5.18). Of the three rare variant alleles, the "2" allele at SNP 13, which is a frameshift mutation denoted "3020insC," demonstrated the greatest association with fibrostenosing disease (47% vs. 17%, $p=0.006$ for cohorts combined). These results indicate that fibrostenosis-predisposing alleles can be linked to the NOD2/CARD15 locus.

As further disclosed herein in Example VI, patients who were carriers of two fibrostenosis-predisposing alleles in NOD2/CARD15 were significantly more likely to have fibrostenosing disease as compared with patients who were not carriers of NOD2/CARD15 mutations at SNP 8, SNP 12 or SNP 13 (85% vs. 43%; odds ratio 7.4; 95% confidence interval 1.9-28.9, $p=0.004$). See FIG. 3. Patients who were carriers of a single NOD2/CARD15 fibrostenosis-predisposing allele were also significantly more likely to have fibrostenosing disease when compared with patients who were not carriers of any of the three NOD2/CARD15 fibrostenosis-predisposing alleles assayed (64% vs. 43%; odds ratio 2.37; 95% confidence interval 1.26-4.47; $p=0.008$). These results confirm that patients who have a fibrostenosis-predisposing allele linked to a NOD2/CARD15 locus can have the fibrostenosing subtype of Crohn's disease and further indicate that Crohn's disease patients with multiple fibrostenosis-predisposing alleles (homozygous mutations or compound heterozygous mutations) linked to NOD2/CARD15 have an increased risk of fibrostenosing disease as compared to individuals carrying a single fibrostenosis-predisposing allele.

Figure 4:
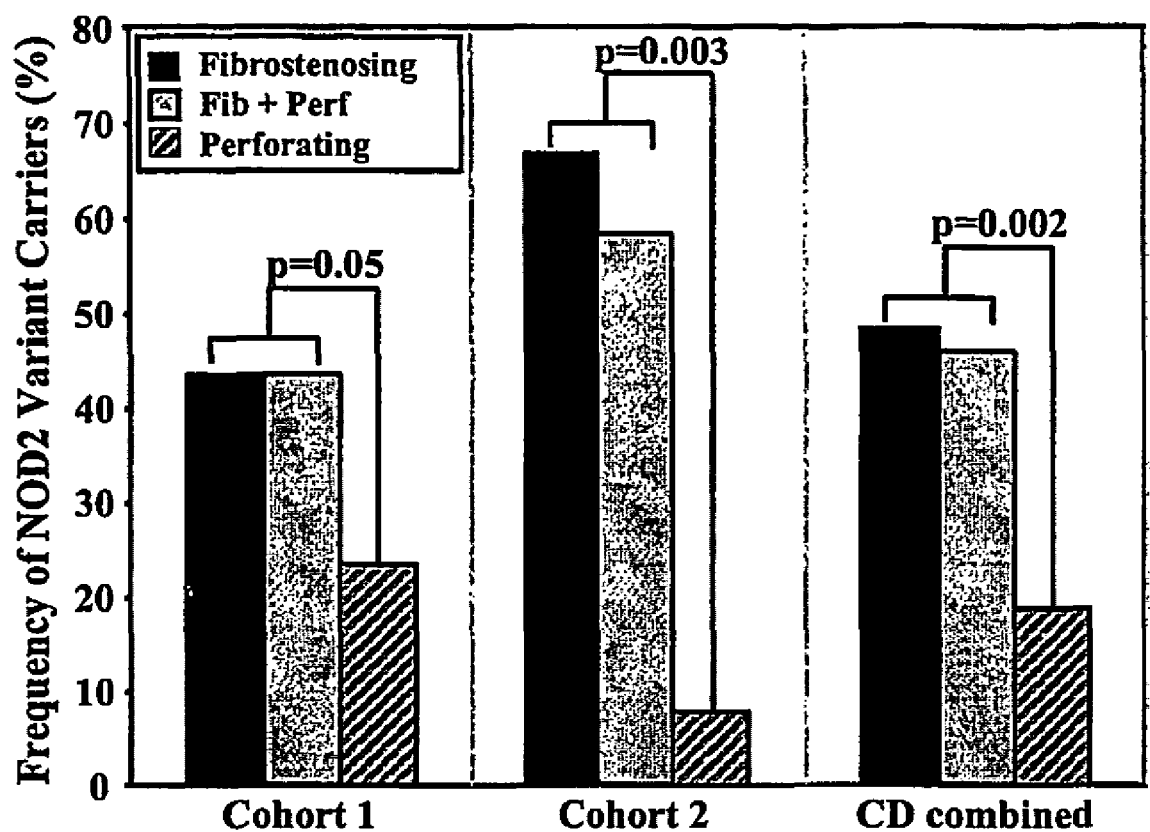
FIG. 4 shows a comparison of NOD2/CARD15 variant allelic frequencies in patients with fibrostenosing disease compared with perforating disease.

Fibrostenosing and perforating disease can occur together in the same patient. Patients with fibrostenosing disease can be characterized, for example, as i) having only fibrostenosing disease or ii) having both fibrostenosing and perforating disease. As disclosed herein in Example VII, the percentage of patients having only fibrostenosing disease that carried a "2" allele at SNP 8, SNP 12, or SNP 13 of the NOD2/CARD15 locus was 48.3%, which was similar to that seen in patients with both fibrostenosing and perforating complications (46.0%; p=0.8). As seen in FIG. 4, when patients with fibrostenosing disease were compared with those patients described as having perforating disease only (perianal or internal), the frequency of the "2" allele at SNP 8, SNP 12 or SNP 13 of the NOD2/CARD15 locus in patients with fibrostenosing disease (with or without perforating complications) was significantly greater than that seen in patients with only perforating complications (46.6% versus 18.6%; p=0.002).

As further disclosed herein in Example VIII, multivariant analysis was performed to investigate the association of a "2" allele at SNP 8, SNP 12, or SNP 13 of the NOD2/CARD15 locus with clinical phenotypes. For multivariant analysis, all variables with at least borderline significance (p<0.1) in either cohort were tested simultaneously for their association with a "2" allele at SNP 8, SNP 12, or SNP 13 of the NOD2/CARD15 locus using logistic regression. As shown in Table 7, the clinical phenotype of fibrostenosing disease was significantly associated (p<0.05) with these rare alleles at the NOD2/CARD15 locus (odds ratio 2.8; 95% confidence interval, 1.3-6.0). These results confirm that fibrostenosing disease is independently associated with a "2" allele at SNP 8, SNP 12, or SNP 13 of the NOD2/CARD15 locus.

Because fibrostenosing disease is more likely to occur in patients with small-bowel involvement, patients were stratified on the basis of small-bowel involvement to analyze whether the association between fibrostenosing disease and NOD2/CARD15 variant alleles was a primary association (see Example IX). Among patients with small-bowel involvement, 26.4% of patients who did not have fibrostenosing disease (n=53) had a "2" allele at SNP 8, SNP 12, or SNP 13, whereas 46.1% of patients who had fibrostenosing disease (n=102) had a "2" allele at SNP 8, SNP 12, or SNP 13 (p=0.017). A similar trend was observed among patients without small-bowel involvement (p=0.05), and the combined analysis conditioning on small-bowel involvement yielded a significance level of 0.009. After controlling for fibrostenosing disease, small-bowel involvement was not associated with a "2" allele at SNP 8, SNP 12, or SNP 13 of the NOD2/CARD15 locus (p=0.63). This result agrees with the results from logistic regression analysis (see Example VIII) and indicates that the association between fibrostenosing disease and a "2" allele at SNP 8, SNP 12, or SNP 13 of the NOD2/CARD15 locus is independent of small-bowel involvement. These results further indicate that the observed small-bowel association with a "2" allele at SNP 8, SNP 12, or SNP 13 of the NOD2/CARD15 locus is secondary to the presence of fibrostenosing disease.

Based on these discoveries, the present invention provides a method of diagnosing or predicting susceptibility to a clinical subtype of Crohn's disease characterized by fibrostenosing disease by determining the presence or absence in an individual of a fibrostenosis-predisposing allele linked to a NOD2/CARD15 locus, where the presence of the fibrostenosis-predisposing allele is diagnostic of or predictive of susceptibility to the clinical subtype of Crohn's disease characterized by fibrostenosing disease. The methods of the invention can be advantageous in that they are noninvasive and can be conveniently practiced, for example, with a blood sample from an individual. The methods of the invention can be used to quickly, easily and reliably diagnose or predict susceptibility to a clinical subtype of Crohn's disease characterized by fibrostenosing disease as described further herein below.

In one embodiment, a method of the invention is practiced with a fibrostenosis-predisposing allele located within the NOD2/CARD15 locus. In another embodiment, NF-kappa B activation by a NOD2/CARD15 polypeptide encoded by the fibrostenosis-predisposing allele is reduced as compared to NF-kappa B activation by a wild-type NOD2/CARD15 polypeptide. In a further embodiment, a method of the invention is practiced with a fibrostenosis-predisposing allele located in a coding region of the NOD2/CARD15 locus, for example, within a region encoding residues 744 to 1020 of NOD2/CARD15. In still a further embodiment, a method of the invention is practiced with a fibrostenosis-predisposing allele which is a "2" allele at SNP 8, SNP 12, or SNP 13. In yet a further embodiment, a method of the invention is practiced with a fibrostenosis-predisposing allele which is a "2" allele at SNP 13. In another embodiment, a method of the invention is practiced with a fibrostenosis-predisposing allele which is located in a non-coding region of the NOD2/CARD15 locus. Such an allele can be, without limitation, a JW1, JW15, or JW16 variant allele. In another embodiment, a method of the invention is practiced with a fibrostenosis-predisposing allele which is located in a promoter region of the NOD2/CARD15 locus. Useful fibrostenosis-predisposing alleles in the promoter region of NOD2/CARD15 include, but are not limited to, JW17 and JW18 variant alleles.

The present invention relates to genetic markers which localize to the IBD1 locus on chromosome 16. Utilizing genome wide scan linkage strategies, the IBD1 locus was mapped to the proximal region of the long arm of chromosome 16 (16q12) in the Caucasian population (Hugot et al., *Nature* 379:821-823 (1996)). This finding has been replicated in many studies, including an international collaborative study reporting a high multipoint linkage score (MLS) for a complex disease (MLS=5.7 at marker D16S411 in 16q12). See Cho et al., *Inflamm. Bowel Dis.* 3:186-190 (1997), Akolkar et al., *Am. J. Gastroenterol.* 96:1127-1132 (2001), Ohmen et al., *Hum. Mol. Genet.* 5:1679-1683 (1996), Parkes et al., *Lancet* 348:1588 (1996), Cavanaugh et al., *Ann. Hum. Gent.* (1998), Brant et al., *Gastroenterology* 115:1056-1061 (1998), Curran et al., *Gastroenterlology* 115:1066-1071 (1998), Hampe et al., *Am. J. Hum. Genet.* 64:808-816 (1999), and Annese et al., *Eur. J. Hum. Genet.* 7:567-573 (1999). NOD2/CARD15 within the IBD1 locus was simultaneously identified by a positional-cloning strategy (Hugot et al., *Nature* 411:599-603 (2001)) and a positional candidate gene strategy (Ogura et al., *Nature* 411:603-606 (2001), Hampe et al., *Lancet* 357:1925-1928 (2001)). The encoded NOD2/CARD15 protein contains amino-terminal caspase recruitment domains (CARDs), which can activate NF-kappa B (NF-κB), and several carboxy-terminal leucine-rich repeat domains (Ogura et al, *J. Biol. Chem.* 276:4812-4818 (2001)). FIG. 1 shows an illustration of the NOD2/CARD15 locus.

The sequence of the human NOD2/CARD15 gene can be found in GenBank as accession number NM_022162, which is incorporated by reference herein. In addition, the complete sequence of human chromosome 16 clone RP11-327F22, which includes NOD2/CARD15, can be found in GenBank as accession number AC007728, which is incorporated by reference herein. Furthermore, the sequence of NOD2/CARD15 from other species can be found in the GenBank database.

Variations at three single nucleotide polymorphisms in the coding region of NOD2/CARD15 have been previously described. These three SNPs, designated SNP 8, SNP 12 and SNP 13, are located in the carboxy-terminal region of the NOD2/CARD15 gene (Hugot et al., supra, 2001).

The invention relies, in part, on determining the presence or absence in an individual of a fibrostenosing-predisposing allele linked to a NOD2/CARD15 locus. The term "fibrostenosis-predisposing allele," as used herein, means a stably heritable molecular variation that is linked to the NOD2/CARD15 locus and that tends to be inherited together with the clinical subtype of Crohn's disease characterized by fibrostenosing disease more often than would be expected according to traditional Mendelian genetics. A fibrostenosis-predisposing allele useful in the invention can be, without limitation, a single nucleotide polymorphism (SNP), microsatellite (ms), variable number tandem repeat (VNTR) polymorphism, or a substitution, insertion or deletion of one or more nucleotides. One skilled in the art understands that a fibrostenosis-predisposing allele also can be a molecular variation such as abnormal methylation or other modification that does not produce a difference in the primary nucleotide sequence of the fibrostenosis-predisposing allele as compared to the wild type allele.

The term "linked to," as used herein in reference to a fibrostenosis-predisposing allele and a NOD2/CARD15 locus, means that the fibrostenosis-predisposing allele and the NOD2/CARD15 locus are inherited together more often than would be expected according to traditional Mendelian genetics. It is understood that an allele and locus are linked when there is less than 50% recombination between the two sites. A fibrostenosis-predisposing allele is generally separated from a NOD2/CARD15 locus by at most 50 centiMorgan (cM). As non-limiting examples, a fibrostenosis-predisposing allele can be within 50 centiMorgan (cM), 40 cM, 30 cM, 20 cM, 10 cM, 5 cM, or 1 cM of the NOD2/CARD15 locus. The distance between a linked fibrostenosis-predisposing allele and a NOD2/CARD15 locus can also be, for example, 50,000,000 base pairs (bps), 40,000,000 bps, 30,000,000 bps, 20,000,000 bps, 10,000,000 bps, 5,000,000 bps, 1,000,000 bps, 500,000 bps, 100,000 bps, 50,000 bps, 10,000 bps, 1,000 bps or 100 bps.

The methods of the invention are useful for diagnosing or predicting susceptibility to a clinical subtype of Crohn's disease (regional enteritis), which is a disease of chronic inflammation that can involve any part of the gastrointestinal tract. Commonly the distal portion of the small intestine (ileum) and cecum are affected in Crohn's disease. In other cases, the disease is confined to the small intestine, colon or anorectal region. Crohn's disease occasionally involves the duodenum and stomach, and more rarely the esophagus and oral cavity.

The variable clinical manifestations of Crohn's disease are, in part, a result of the varying anatomic localization of the disease. The most frequent symptoms of Crohn's disease are abdominal pain, diarrhea and recurrent fever. Crohn's disease is commonly associated with intestinal obstruction or fistula, which is an abnormal passage, for example, between diseased loops of bowel. Crohn's disease also can include extra-intestinal complications such as inflammation of the eye, joints and skin; liver disease; kidney stones or amyloidosis; and is associated with an increased risk of intestinal cancer.

Several features are characteristic of the pathology of Crohn's disease. The inflammation associated with Crohn's disease, known as transmural inflammation, involves all layers of the bowel wall. Thickening and edema, for example, typically appear throughout the bowel wall, with fibrosis also present in long-standing disease. The inflammation characteristic of Crohn's disease also is discontinuous, with segments of inflamed tissue, known as "skip lesions," separated by apparently normal intestine. Furthermore, linear ulcerations, edema, and inflammation of the intervening tissue lead to a "cobblestone" appearance of the intestinal mucosa, which is distinctive of Crohn's disease.

A hallmark of Crohn's disease is the presence of discrete aggregations of inflammatory cells, known as granulomas, which are generally found in the submucosa. About half of Crohn's disease cases display the typical discrete granulomas, while others show a diffuse granulomatous reaction or nonspecific transmural inflammation. As a result, the presence of discrete granulomas is indicative of Crohn's disease, although the absence granulomas also is consistent with the disease. Thus, transmural or discontinuous inflammation, rather than the presence of granulomas, is a preferred diagnostic indicator of Crohn's disease (Rubin and Farber, *Pathology* (Second Edition) Philadelphia: J.B. Lippincott Company (1994)).

Crohn's disease is a classification representing a number of heterogeneous disease subtypes that affect the gastrointestinal tract and may produce similar symptoms. As non-limiting examples, patients with Crohn's disease can be characterized as having subtypes characterized by fibrostenosing disease, internal-perforating disease, perianal fistulizing disease or ulcerative colitis (UC)-like disease based on previously described criteria (Gasche et al., *Inflammatory Bowel Diseases* 6:8-15 (2000); Vasiliauskas et al., *Gut* 47:487-496 (2000); Vasiliauskas et al., *Gastroenterology* 110:1810-1819 (1996); and Greenstein et al., *Gut* 29:588-592 (1988)).

According to well-established criteria fibrostenosing disease is defined by documented persistent intestinal obstruction or an intestinal resection for an intestinal obstruction. Radiographic, endoscopic, surgical or histopathological documentation can be used to confirm a diagnosis of the fibrostenosing subtype of Crohn's disease. The fibrostenosing subtype of Crohn's disease can be accompanied by other symptoms such as perforations, abscesses or fistulae. In addition, the fibrostenosing subtype of Crohn's disease can be characterized by persistent symptoms of intestinal blockage such as nausea, vomiting, abdominal distention and inability to eat solid food. Intestinal X-rays of patients with the fibrostenosing subtype of Crohn's disease can show, for example, distention of the bowel before the point of blockage.

Additional subtypes of Crohn's disease can be identified using defined clinical criteria. For example, internal perforating disease can be defined as current or previous evidence of entero-enteric or entero-vesicular fistulae, intraabdominal abscesses, or small bowel perforation. Perianal perforating disease can be defined by current or previous evidence of either perianal fistulae or abscesses or rectovaginal fistula. UC-like disease can be defined by current or previous evidence of left-sided colonic involvement, symptoms of bleeding or urgency, and crypt abscesses on colonic biopsies as previously described. Disease location can be classified as small bowel, colon, or both based on one or more endoscopic, radiologic or pathologic studies.

The fibrostenosing subtype of Crohn's disease can occur in patients having disease with small-bowel involvement. As disclosed herein, after controlling for fibrostenosing disease, small-bowel involvement was not associated with a "2" allele at SNP 8, SNP 12, or SNP 13 of the NOD2/CARD15 locus ($p=0.63$; see Example IX). This result agrees with the results from logistic regression analysis disclosed in Example VIII and indicates that the association between fibrostenosing disease and a "2" allele at SNP 8, SNP 12, or SNP 13 of the NOD2/CARD15 locus is independent of small-bowel involvement. Based on these findings, the present invention provides a method of diagnosing or predicting susceptibility to a clinical subtype of Crohn's disease characterized by fibrostenosing disease independent of small bowel involvement by determining the presence or absence in an individual of a fibrostenosis-predisposing allele linked to a NOD2/CARD15 locus, where the presence of the fibrostenosis-predisposing allele is diagnostic of or predictive of susceptibility to the clinical subtype of Crohn's disease characterized by fibrostenosing disease independent of small bowel involvement.

The diagnostic methods of the invention are practiced in an individual. As used herein, the term "individual" means an animal, such as a human or other mammal, capable of having the fibrostenosing subtype of Crohn's disease. An individual can have one or more symptoms of Crohn's disease or the fibrostenosing subtype of Crohn's disease or can be asymptomatic. The methods of the invention can be useful, for example, for diagnosing the fibrostenosing subtype of Crohn's disease in an individual with one or more symptoms, or for predicting susceptibility to the fibrostenosing subtype of Crohn's disease in an asymptomatic individual such as an individual at increased risk for having the fibrostenosing subtype of Crohn's disease. In one embodiment, the methods of the invention are used to determine the presence or absence of the fibrostenosing subtype of Crohn's disease in an individual known to have Crohn's disease.

The methods of the invention can be useful, for example, to diagnose or predict susceptibility to the fibrostenosing subtype of Crohn's disease in an Ashkenazi Jewish individual. Crohn's disease is significantly more common (2 to 8 fold higher) in Ashkenazi Jews than in non-Jewish Caucasians (Brant et al., *Gastroenterol.* 115:1056-1061 (1998)). Furthermore, among persons of Jewish ethnicity, American or European Ashkenazi Jews have a 2 to 4 fold increased risk of having this inflammatory bowel disease compared with Sephardic or Oriental Jews (Yang and Rotter in Kirschner and Shorter (Eds.), *Inflammatory Bowel Disease* Baltimore: Williams and Wilkins, p. 301-331 (1995); Rozen et al., *Gastroenterol.* 76:25-30 (1979)). The empiric risk of Crohn's disease for a first degree relative of a proband with Crohn's disease is 7.8% for Jews compared with 5.2% for non-Jews (p=0.005; Yang et al., *Gut* 34:517-524 (1993)). Thus, the Jewish population and especially the Ashkenazi Jewish population represents a group at increased risk for Crohn's and autoimmune diseases of related etiology.

The methods of the invention rely on fibrostenosis-predisposing alleles linked to the NOD2/CARD15 locus. NOD2/CARD15 has structural homology with both apoptosis regulators Apaf-1/CED-4 and a class of plant disease resistant gene products (Ogura et al., *J. Biol. Chem,* 276:4812-4818 (2001)). Similar to plant disease resitant gene products, NOD2/CARD15 has an amino-terminal effector domain, a nucleotide-binding domain and leucine rich repeats (LRRs). Wild-type NOD2/CARD15 activates nuclear factor NF-kappa B, making it responsive to bacterial lipopolysaccharides (LPS; Ogura et al., *J. Biol. Chem,* 276:4812-4818 (2001); Inohara et al., *J. Biol. Chem.* 276:2551-2554 (2001). NOD2/CARD15 can function as an intercellular receptor for LPS, with the leucine rich repeats required for responsiveness. Like NOD2/CARD15, cytosolic plant disease resistant polypeptides have carboxy-terminal leucine rich repeats that are important for the recognition of pathogen components and induction of pathogen-specific responses (Parniske et al., *Cell* 91:821-832 (1997); Ellis et al., *Plant Cell* 11:495-506 (1999); Dixon et al., *Proc. Natl. Acad. Sci. USA* 97: 8807-8814 (2000)).

In one embodiment, the fibrostenosis-predisposing allele is located within the NOD2/CARD15 locus, a schematic of which is shown in FIG. 1. The NOD2/CARD15 locus includes coding regions of the NOD2/CARD15 gene as well as non-coding regions such as introns and 5' and 3' untranslated regions. One skilled in the art understands that the NOD2/CARD15 locus can include, for example, promoter regions 5' of the gene, enhancer regions 5' or 3' of the gene or in intronic sequences, and mRNA stability regions 3' of the gene.

In another embodiment, the fibrostenosis-predisposing allele is located in a coding region of the NOD2/CARD15 locus, for example within a region encoding residues 744 to 1020 of NOD2/CARD15. Residues 744 to 1020 of the NOD2/CARD15 polypeptide contain several leucine-rich repeats in the carboxy-terminal portion of the NOD2/CARD15 polypeptide. Fibrostenosis-predisposing alleles located in a region encoding residues 744 to 1020 of NOD2/CARD15 include, without limitation, SNP 12 and SNP 13. A fibrostenosis-predisposing allele useful in the invention also can be an allele which encodes a NOD2/CARD15 polypeptide with reduced NF-kappa B activation as compared to NF-kappa B activation by a wild-type NOD2/CARD15 polypeptide. As an example, a rare variant allele at SNP 13 results in a truncated NOD2/CARD15 polypeptide which has reduced ability to induce NF-kappa B in response to LPS stimulation (Ogura et al., *Nature* 411:603-606 (2001)).

A fibrostenosis-predisposing allele useful in the invention can be, for example, a "2" allele at SNP 8, SNP 12 or SNP 13. SNP 8, SNP 12, and SNP 13 are located within the coding region of NOD2/CARD15 as shown in FIG. 1. In one embodiment, a method of the invention is practiced with a fibrostenosis-predisposing allele which is the SNP 8 "2" allele. As used herein, the term "SNP 8" means a single nucleotide polymorphism within exon 4 in the NOD2/CARD15 gene, which occurs within a triplet encoding amino acid 702 of the NOD2/CARD15 protein. The "1" allele, in which cytosine (c) resides at position 138,991 of the AC007728 sequence, is the common or "wild-type" SNP 8 allele and occurs within a triplet encoding an arginine at amino acid 702. The "2" allele of SNP 8, in which thymine (t) resides at position 138,991 of the AC007728 sequence, is a rare variant that results in an arginine (R) to tryptophan (W) substitution at amino acid 702 of the NOD2/CARD15 protein. Accordingly, the rare "2" allele at SNP 8 is denoted "R702W" or "702W" and can also be denoted "R675W" based on the earlier numbering system of Hugot et al., supra, 2001. The NCBI SNP ID number for SNP 8 is rs2066844, which is incorporated herein by reference. As disclosed herein and described further below, the presence of allele "1" or "2" at SNP 8, or another SNP described below, can be conveniently detected, for example, by allelic discrimination assays or sequence analysis.

A method of the invention also can be practiced with a fibrostenosis-predisposing allele which is the SNP 12 "2" allele. As used herein, the term "SNP 12" means a single nucleotide polymorphism within exon 8 in the NOD2/CARD15 gene, which occurs within a triplet encoding amino acid 908 of the NOD2/CARD15 protein. The "1" allele, in which guanine (g) resides at position 128,377 of the AC007728 sequence, is the common or "wild-type" SNP 12 allele and occurs within a triplet encoding glycine at amino acid 908. The "2" allele of SNP 12, in which cytosine (c) resides at position 128,377 of the AC007728 sequence, is a rare variant that results in a glycine (G) to arginine (R) substitution at amino acid 908 of the NOD2/CARD15 protein. This rare "2" allele at SNP 12 is denoted "G908R" or "908R" and can also be denoted "G881R" based on the earlier numbering system of Hugot et al., supra, 2001. SNP 12 is located within the leucine rich repeat region of the NOD2/CARD15 gene. The NCBI SNP ID number for SNP 12 is rs2066845, which is incorporated herein by reference.

A method of the invention also can be practiced with a fibrostenosis-predisposing allele which is the SNP 13 "2" allele. This allele is an insertion of a single nucleotide that results in a frame shift in the tenth leucine-rich repeat of the NOD2/CARD15 protein and is followed by a premature stop codon. The resulting truncation of the NOD2/CARD15 protein appears to prevent activation of NF-kB in response to bacterial lipopolysaccharides (Ogura et al., supra, 2001). As used herein, the term "SNP 13" means a single nucleotide polymorphism within exon 11 in the NOD2/CARD15 gene, which occurs in a triplet encoding amino acid 1007 of the NOD2/CARD15 protein. The "2" allele of SNP 13, in which a cytosine has been added at position 121,139 of the AC007728 sequence, is a rare variant resulting in a frame shift mutation at amino acid 1007. Accordingly, the rare "2" allele at SNP 13 is denoted "1007fs" and can also be denoted "3020insC," or "980fs" based on the earlier numbering system of Hugot et al., supra, 2001. The NCBI SNP ID number for SNP 13 is rs2066847, which is incorporated herein by reference.

One skilled in the art recognizes that a particular polymorphic allele can be conveniently defined, for example, in comparison to a Centre d'Etude du Polymorphisme Humain (CEPH) reference individual such as the individual designated 1347-02 (Dib et al., *Nature* 380:152-154 (1996)), using commercially available reference DNA obtained, for example, from PE Biosystems (Foster City, Calif.). In addition, specific information on SNPs can be obtained from the dbSNP of the National Center for Biotechnology Information (NCBI).

A fibrostenosis-predisposing allele also can be located in a non-coding region of the NOD2/CARD15 locus. Non-coding regions include, for example, intron sequences as well as 5' and 3' untranslated sequences. Examples of a fibrostenosis-predisposing allele in an intron sequence of the NOD2/CARD15 gene include, but are not limited to, the JW1 variant allele, which is described below. Examples of fibrostenosis-predisposing alleles located in the 3' untranslated region of the NOD2/CARD15 gene include, without limitation, JW15 and JW16 variant alleles, which are described below. Examples of fibrostenosis-predisposing alleles located in the 5' untranslated region of the NOD2/CARD15 gene include, without limitation, the JW17 and JW18 variant alleles, which are described below; In one embodiment, a method of the invention is practiced with a fibrostenosis-predisposing allele located in a non-coding region of the NOD2/CARD15 locus which is a JW1, JW15 or JW16 variant allele. In another embodiment, a method of the invention is practiced with a fibrostenosis-predisposing allele located in a promoter region of the NOD2/CARD15 locus which is a JW17 or JW18 variant allele.

As used herein, the term "JW1 variant allele" means a genetic variation at nucleotide 158 of intervening sequence 8 (intron 8) of a NOD2/CARD15 gene. In relation to the AC007728 sequence, the JW1 variant is located at position 128,143. The genetic variation at nucleotide 158 of intron 8 can be, but is not limited to, a single nucleotide substitution, multiple nucleotide substitutions, or a deletion or insertion of one or more nucleotides. The wild type sequence of intron 8 has a cytosine at position 158; as non-limiting examples, a JW1 variant allele can have a cytosine (C) to adenine (A), cytosine to guanine (G), or cytosine to thymine (T) substitution at nucleotide 158 of intron 8. In one embodiment, the JW1 variant allele is a change from a cytosine to a thymine at nucleotide 158 of NOD2/CARD15 intron 8.

As used herein, the term "JW15 variant allele" means a genetic variation in the 3' untranslated region of NOD2/CARD15 at nucleotide position 118,790 of the AC007728 sequence. The genetic variation at nucleotide 118,790 can be, but is not limited to, a single nucleotide substitution, multiple nucleotide substitutions, or a deletion or insertion of one or more nucleotides. The wild type sequence has an adenine (A) at position 118,790; as non-limiting examples, a JW15 variant allele can have an adenine (A) to cytosine (C), adenine to guanine (G), or adenine to thymine (T) substitution at nucleotide 118,790. In one embodiment, the JW15 variant allele is a change from an adenine to a cytosine at nucleotide 118,790.

As used herein, the term "JW16 variant allele" means a genetic variation in the 3' untranslated region of NOD2/CARD15 at nucleotide position 118,031 of the AC007728 sequence. The genetic variation at nucleotide 118,031 can be, but is not limited to, a single nucleotide substitution, multiple nucleotide substitutions, or a deletion or insertion of one or more nucleotides. The wild type sequence has a guanine (G) at position 118,031; as non-limiting examples, a JW16 variant allele can have a guanine (G) to cytosine (C), guanine to adenine (A), or guanine to thymine (T) substitution at nucleotide 118,031. In one embodiment, the JW16 variant allele is a change from a guanine to an adenine at nucleotide 118,031.

As used herein, the term "JW17 variant allele" means a genetic variation in the 5' untranslated region of NOD2/CARD15 at nucleotide position 154,688 of the AC007728 sequence. The genetic variation at nucleotide 154,688 can be, but is not limited to, a single nucleotide substitution, multiple nucleotide substitutions, or a deletion or insertion of one or more nucleotides. The wild type sequence has a cytosine (C) at position 154,688; as non-limiting examples, a JW17 variant allele can have a cytosine (C) to guanine (G), cytosine to adenine (A), or cytosine to thymine (T) substitution at nucleotide 154,688. In one embodiment, the JW17 variant allele is a change from a cytosine to a thymine at nucleotide 154,688.

As used herein, the term "JW18 variant allele" means a genetic variation in the 5' untranslated region of NOD2/CARD15 at nucleotide position 154,471 of the AC007728 sequence. The genetic variation at nucleotide 154,471 can be, but is not limited to, a single nucleotide substitution, multiple nucleotide substitutions, or a deletion or insertion of one or more nucleotides. The wild type sequence has a cytosine (C) at position 154,471; as non-limiting examples, a JW18 variant allele can have a cytosine (C) to guanine (G), cytosine to adenine (A), or cytosine to thymine (T) substitution at nucleotide 154,471. In one embodiment, the JW18 variant allele is a change from a cytosine to a thymine at nucleotide 154,471.

Further provided herein is a method of diagnosing or predicting susceptibility to a clinical subtype of Crohn's disease characterized by fibrostenosing disease by determining the presence or absence in an individual of at least two fibrostenosis-predisposing alleles linked to a NOD2/CARD15 locus, where the presence of one or more of the fibrostenosis-predisposing alleles is diagnostic of or predictive of susceptibility to the clinical subtype of Crohn's disease characterized by fibrostenosing disease. In a method of the invention, the at least two fibrostenosis-predisposing alleles are "2" alleles at SNP 8, SNP 12 or SNP 13.

Further provided herein is a method of diagnosing or predicting susceptibility to a clinical subtype of Crohn's disease characterized by fibrostenosing disease by determining the presence or absence in an individual of at least two fibrostenosis-predisposing alleles linked to a NOD2/CARD15 locus, where the presence of one or more of the fibrostenosis-predisposing alleles is diagnostic of or predictive of susceptibility to the clinical subtype of Crohn's disease characterized by fibrostenosing disease. In one embodiment, the at least two fibrostenosis-predisposing alleles are "2" alleles at SNP 8, SNP 12, or SNP 13. In another embodiment, a method of the invention for diagnosing or predicting susceptibility to a clinical subtype of Crohn's disease characterized by fibrostenosing disease is practiced by determining the presence or absence in the individual of (i) a "2" allele at SNP 8, (ii) a "2" allele at SNP 12, and (iii) a "2" allele at SNP 13, where the presence of one or more of the "2" alleles at SNP 8, SNP 12, and SNP 13 is diagnostic of or predictive of susceptibility to the clinical subtype of Crohn's disease characterized by fibrostenosing disease.

The strength of the association between a fibrostenosing-predisposing allele and Crohn's disease can be characterized by a particular odds ratio such as an odds ratio of at least 2 with a lower 95% confidence interval limit of greater than 1. Such an odds ratio can be, for example, at least 3.0, 4.0, 5.0, 6.0, 7.0, or 8.0 or greater with a lower 95% confidence interval limit of greater than 1, such as an odds ratio of at least 7.4 with a 95% confidence interval of 1.9-28.9 (see FIG. 3). In addition, an odds ratio can be, for example, at least 2.37 with a lower confidence interval limit of 1.26-4.47 (see FIG. 3). In one embodiment, the fibrostenosis-predisposing allele is associated with the clinical subtype of Crohn's disease characterized by fibrostenosing disease with an odds ratio of at least 2 and a lower 95% confidence limit greater than 1. Methods for determining an odds ratio are well known in the art (see, for example, Schlesselman et al., *Case Control Studies: Design, Conduct and Analysis* Oxford University Press, New York (1982)).

In one embodiment, a fibrostenosis-predisposing allele is associated with the fibrostenosing subtype of Crohn's disease with a p value of equal to or less than 0.05. In other embodiments, a fibrostenosis-predisposing allele is associated with the fibrostenosing subtype of Crohn's disease with a p value of equal to or less than 0.1. As used herein, the term "p value" is synonymous with "probability value." As is well known in the art, the expected p value for the association between a random allele and disease is 1.00. A p value of less than about 0.05 indicates that the allele and disease do not appear together by chance but are influenced by positive factors. Generally, the statistical threshold for significance of linkage has been set at a level of allele sharing for which false positives would occur once in twenty genome scans (p=0.05). In particular embodiments, a fibrostenosis-predisposing allele is associated with a clinical subtype of Crohn's disease characterized by fibrostenosis with a p value of equal to or less than 0.1, 0.05, 0.04, 0.03, 0.02, 0.01, 0.009, 0.008, 0.007, 0.006, 0.005, 0.004, 0.003, 0.002 or 0.001, or with a p value of less than 0.00095, 0.0009, 0.00085, 0.0008 or 0.0005. It is recognized that, in some cases, p values may need to be corrected, for example, to account for factors such as sample size (number of families), genetic heterogeneity, clinical heterogeneity, or analytical approach (parametric or nonparametric method).

A variety of means can be used to determine the presence or absence of a fibrostenosing-predisposing allele in a method of the invention. As an example, enzymatic amplification of nucleic acid from an individual can be conveniently used to obtain nucleic acid for subsequent analysis. The presence or absence of a fibrostenosis-predisposing allele also can be determined directly from the individual's nucleic acid without enzymatic amplification.

Analysis of nucleic acid from an individual, whether amplified or not, can be performed using any of various techniques. Useful techniques include, without limitation, polymerase chain reaction based analysis, sequence analysis and electrophoretic analysis, which can be used alone or in combination. As used herein, the term "nucleic acid" means a polynucleotide such as a single-or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule. It is understood that such nucleic acid can be attached to a synthetic material such as a bead or column matrix.

The presence or absence of a fibrostenosing-predisposing allele can involve amplification of an individual's nucleic acid by the polymerase chain reaction. Use of the polymerase chain reaction for the amplification of nucleic acids is well known in the art (see, for example, Mullis et al. (Eds.), *The Polymerase Chain Reaction*, Birkhäuser, Boston, (1994)). In one embodiment, polymerase chain reaction amplification is performed using one or more fluorescently labeled primers. In another embodiment, polymerase chain reaction amplification is performed using one or more labeled or unlabeled primers that contain a DNA minor grove binder.

Several different primers can be used to amplify an individual's nucleic acid by the polymerase chain reaction. For example, the PCR primers listed in Table 2 (SEQ ID NOS: 37-44) and shown in FIGS. 5 to 8 can be used to amplify specific regions in the NOD2/CARD15 locus of an individual's nucleic acid. For example, the region surrounding SNP 8 can be amplified using SEQ ID NO: 39 and 40; SNP 12 can be amplified using SEQ ID NOS: 41 and 42, and the region surrounding SNP 13 can be amplified using SEQ ID NOS: 43 and 44. In addition, for example, the region surrounding. As understood by one skilled in the art, additional primers for PCR analysis can be designed based on the sequence flanking the region of interest. As a non-limiting example, a sequence primer can contain about 15 to 30 nucleotides of a sequence upstream or downstream of the region of interest. Such primers are generally designed to have sufficient guanine and cytosine content to attain a high melting temperature which allows for a stable annealing step in the amplification reaction. Several computer programs, such as Primer Select, are available to aid in the design of PCR primers.

A Taqman® allelic discrimination assay available from Applied Biosystems can be useful for determining the presence or absence of a fibrostenosing-predisposing allele. In a Taqman® allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonance energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., *Nuc. Acids Research* 28:655-661

(2000). Minor grove binders include, but are not limited to, compounds such as dihydrocyclopyrroloindole tripeptide (DPI3).

Sequence analysis also can be useful for determining the presence or absence of a fibrostenosing-predisposing allele in a method of the invention. A fibrostenosing-predisposing allele can be detected by sequence analysis using primers disclosed herein, for example, as the PCR primers listed in Table 2 (SEQ ID NOS: 37-44) and shown in FIGS. 5 to 8. As understood by one skilled in the art, additional primers for sequence analysis can be designed based on the sequence flanking the region of interest. As a non-limiting example, a sequence primer can contain about 15 to 30 nucleotides of a sequence about 40 to 400 base pairs upstream or downstream of the region of interest. Such primers are generally designed to have sufficient guanine and cytosine content to attain a high melting temperature which allows for a stable annealing step in the sequencing reaction.

The term "sequence analysis," as used herein in reference to one or more nucleic acids, means any manual or automated process by which the order of nucleotides in the nucleic acid is determined. As an example, sequence analysis can be used to determine the nucleotide sequence of a sample of DNA. The term sequence analysis encompasses, without limitation, chemical and enzymatic methods such as dideoxy enzymatic methods including, for example, Maxam-Gilbert and Sanger sequencing as well as variations thereof. The term sequence analysis further encompasses, but is not limited to, capillary array DNA sequencing, which relies on capillary electrophoresis and laser-induced fluorescence detection and can be performed using instruments such as the MegaBACE 1000 or ABI 3700. As additional non-limiting examples, the term sequence analysis encompasses thermal cycle sequencing (Sears et al., *Biotechniques* 13:626-633 (1992)); solid-phase sequencing (Zimmerman et al., *Methods Mol. Cell. Biol.* 3:39-42 (1992); and sequencing with mass spectrometry such as matrix-assisted laser desorption/ionization time-of-flight mass spectrometry MALDI-TOF MS (Fu et al., *Nature Biotech.* 16: 381-384 (1998)). The term sequence analysis also includes, yet is not limited to, sequencing by hybridization (SBH), which relies on an array of all possible short oligonucleotides to identify a segment of sequences present in an unknown DNA (Chee et al., *Science* 274:610-614 (1996); Drmanac et al., *Science* 260:1649-1652 (1993); and Drmanac et al., *Nature Biotech.* 16:54-58 (1998)). One skilled in the art understands that these and additional variations are encompassed by the term sequence analysis as defined herein. See, in general, Ausubel et al., supra, Chapter 7 and supplement 47.

The invention also provides a method of diagnosing or predicting susceptibility to a clinical subtype of Crohn's disease characterized by fibrostenosing disease by determining the presence or absence in an individual of a fibrostenosis-predisposing allele linked to a NOD2/CARD15 locus, where the presence of the fibrostenosis-predisposing allele is diagnostic of or predictive of susceptibility to the clinical subtype of Crohn's disease characterized by fibrostenosing disease, and where the method includes the steps of obtaining material containing nucleic acid including the NOD2/CARD15 locus from the individual. As used herein, the term "material" means any biological matter from which nucleic acid can be prepared. As non-limiting examples, the term material encompasses whole blood, plasma, saliva, cheek swab, or other bodily fluid or tissue that contains nucleic acid. In one embodiment, a method of the invention is practiced with whole blood, which can be obtained readily by non-invasive means and used to prepare genomic DNA, for example, for enzymatic amplification or automated sequencing. In another embodiment, a method of the invention is practiced with tissue obtained from an individual such as tissue obtained during surgery or biopsy procedures.

Electrophoretic analysis also can be useful in the methods of the invention. Electrophoretic analysis, as used herein in reference to one or more nucleic acids such as amplified fragments, means a process whereby charged molecules are moved through a stationary medium under the influence of an electric field. Electrophoretic migration separates nucleic acids primarily on the basis of their charge, which is in proportion to their size, with smaller molecules migrating more quickly. The term electrophoretic analysis includes, without limitation, analysis using slab gel electrophoresis, such as agarose or polyacrylamide gel electrophoresis, or capillary electrophoresis. Capillary electrophoretic analysis generally occurs inside a small-diameter (50-100-m) quartz capillary in the presence of high (kilovolt-level) separating voltages with separation times of a few minutes. Using capillary electrophoretic analysis, nucleic acids are conveniently detected by UV absorption or fluorescent labeling, and single-base resolution can be obtained on fragments up to several hundred base pairs. Such methods of electrophoretic analysis, and variations thereof, are well known in the art, as described, for example, in Ausubel et al., *Current Protocols in Molecular Biology* Chapter 2 (Supplement 45) John Wiley & Sons, Inc. New York (1999).

Restriction fragment length polymorphism (RFLP) analysis also can be useful for determining the presence or absence of a fibrostenosis-predisposing allele in a method of the invention (Jarcho et al. in Dracopoli et al., *Current Protocols in Human Genetics* pages 2.7.1-2.7.5, John Wiley & Sons, New York; Innis et al., (Ed.), *PCR Protocols*, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization also can be used to detect the presence or absence of a fibrostenosis-predisposing allele. Allele-specific oligonucleotide hybridization is based on the use of a labeled oligonucleotide probe having a sequence perfectly complementary, for example, to the sequence encompassing a fibrostenosis-predisposing allele. Under appropriate conditions, the allele-specific probe hybridizes to a nucleic acid containing the fibrostenosis-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a fibrostenosis-predisposing allele by using an allele-specific oligonucleotide primer that is perfectly complementary to the nucleotide sequence of the fibrostenosis-predisposing allele but which has one or more mismatches as compared to other alleles (Mullis et al., supra, 1994). One skilled in the art understands that the one or more nucleotide mismatches that distinguish between the fibrostenosis-predisposing allele and one or more other alleles are often located in the center of an allele-specific oligonucleotide primer to be used in allele-specific oligonucleotide hybridization. In contrast, an allele-specific oligonucleotide primer to be used in PCR amplification generally contains the one or more nucleotide mismatches that distinguish between the disease-associated and other alleles at the 3' end of the primer.

A heteroduplex mobility assay (HMA) is another well known assay that can be used to detect the presence or absence of a fibrostenosis-predisposing allele in a method of the invention. HMA is useful for detecting the presence of a polymorphic sequence since a DNA duplex carrying a mismatch has reduced mobility in a polyacrylamide gel compared to the mobility of a perfectly base-paired duplex (Delwart et al., *Science* 262:1257-1261 (1993); White et al., *Genomics* 12:301-306 (1992)).

The technique of single strand conformational polymorphism (SSCP) also can be used to detect the presence or absence of a fibrostenosis-predisposing allele in a method of the invention (see Hayashi, *Methods Applic.* 1:34-38 (1991)). This technique is used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also can be used to detect a fibrostenosis-predisposing allele in a method of the invention. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a fibrostenosis-predisposing allele are known in the art and useful in the methods of the invention. Other well-known approaches for determining the presence or absence of a fibrostenosis-predisposing allele include, without limitation, automated sequencing and RNAase mismatch techniques (Winter et al., *Proc. Natl. Acad. Sci.* 82:7575-7579 (1985)). Furthermore, one skilled in the art understands that, where the presence or absence of multiple alleles or a fibrostenosis-predisposing haplotype is to be determined, individual alleles can be detected by any combination of molecular methods. See, in general, Birren et al. (Eds.) *Genome Analysis: A Laboratory Manual* Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the invention for diagnosing or predicting susceptibility to a clinical subtype of Crohn's disease characterized by fibrostenosing disease can be practiced using one or any combination of the well known assays described above or known in the art.

The present invention further provides a method of diagnosing or predicting susceptibility to a clinical subtype of Crohn's disease characterized by fibrostenosing disease by determining the presence or absence in an individual of a fibrostenosis-predisposing haplotype, where the presence of the fibrostenosis-predisposing haplotype is diagnostic of or predictive of susceptibility to the clinical subtype of Crohn's disease characterized by fibrostenosing disease. In one embodiment, the fibrostenosis-predisposing haplotype is associated with a clinical subtype of Crohn's disease characterized by fibrostenosing disease with an odds ratio of at least 2 and a lower 95% confidence limit greater than 1. In another embodiment, the fibrostenosis-predisposing haplotype is associated with a clinical subtype of Crohn's disease characterized by fibrostenosing disease with an odds ratio of at least 3, at least 4, at least 5, at least 6, and a lower 95% confidence limit greater than 1.

The term "fibrostenosis-predisposing haplotype," as used herein, means a combination of alleles that tend to be inherited together with the clinical subtype of Crohn's disease characterized by fibrostenosing disease more often than would be expected according to traditional Mendelian genetics. In a method of the invention, the clinical subtype of Crohn's disease can be, for example, characterized by fibrostenosing disease independent of small bowel involvement. In one embodiment, the fibrostenosis-predisposing haplotype includes at least one allele linked to the NOD2/CARD15 locus. In another embodiment, the fibrostenosis-predisposing haplotype includes a fibrostenosis-predisposing allele. In a further embodiment, a fibrostenosis-predisposing haplotype contains, for example, a variant allele at the NOD2/CARD15 locus. In another embodiment, the fibrostenosis-predisposing haplotype includes the "2" allele at SNP 8, SNP 12, or SNP 13. In a further embodiment, the fibrostenosis-predisposing haplotype includes the "2" allele at SNP 13. In still further embodiments, the fibrostenosis-predisposing haplotype includes the "2" allele at SNP 8, SNP 12, and SNP 13. In another embodiment, the fibrostenosis-predisposing haplotype includes a JW1, JW15, JW16, JW17, or JW18 variant allele. One skilled in the art understands that a fibrostenosis-predisposing haplotype can contain alleles that individually are not significantly associated the fibrostenosing subtype of Crohn's disease, so long as the combination of alleles making up the haplotype tend to be inherited together with the fibrostenosing subtype of Crohn's disease more often than would be expected according to traditional Mendelian genetics.

The presence or absence of a fibrostenosis-predisposing haplotype can be accomplished using any of the methods described herein above for determining the presence or absence of a fibrostenosis-predisposing allele. As an example, enzymatic amplification such as polymerase chain reaction amplification, for example, using one or more fluorescently labeled probes or one or more probes containing a DNA minor grove binder can be useful for determining the presence or absence of a fibrostenosis-predisposing haplotype in a method of the invention.

Antibody based methods also can be useful for determining the presence or absence of a fibrostenosis-predisposing allele or fibrostenosis-predisposing haplotype in a method of the invention. As an example, an antibody that is specifically reactive with a polypeptide or fragment thereof encoded by fibrostenosis-predisposing allele can be used to detect the presence or absence of that allele in an individual. Such an antibody can be, for example, specifically reactive with the truncated version of NOD2/CARD15 generated by a "2" allele at SNP 13 but not reactive with full-length or wild type NOD2/CARD15.

Antibodies useful in the methods of the invention include, without limitation, monoclonal and polyclonal antibodies, single chain antibodies, chimeric antibodies, bifunctional or bispecific antibodies, humanized antibodies, human antibodies, and complementary determining region (CDR)-grafted antibodies, including compounds which include CDR or antigen-binding sequences, which differentially bind to a polypeptide or fragment encoded by a fibrostenosis-predisposing allele but not to other, non-predisposing alleles. Antibody fragments, including Fab, Fab', F(ab')$_2$, and Fv, also can be useful in the methods of the invention as can plastic antibodies or molecularly imprinted polymers (MIPs; Haupt and Mosbauch, *TIBTech* 16:468-475 (1998)). Screening assays to determine differential binding specificity of an antibody are well known in the art (see Harlow et al. (Eds), *Antibodies: A Laboratory Manual*; Cold Spring Harbor Laboratory; Cold Spring Harbor, N.Y. (1988)).

Antibodies useful in a method of the invention can be produced using any method well known in the art, using a polypeptide, or immunogenic fragment thereof, encoded by a fibrostenosis-predisposing allele. Immunogenic polypeptides or fragments can be isolated from natural sources, from recombinant host cells, or can be chemically synthesized. Methods for synthesizing such peptides are known in the art as described, for example, in Merrifield, *J. Amer. Chem. Soc.* 85: 2149-2154 (1963); Krstenansky et al., *FEBS Lett.* 211:10 (1987).

Antibodies that differentially bind to polypeptides encoded by fibrostenosis-predisposing alleles of the invention can be labeled with a detection moiety and used to detect the presence, absence or amount of the encoded polypeptide in vivo, in vitro, or in situ. A moiety, such as a fluorescent molecule, can be linked to an antibody for use in a method of the invention. A moiety such as detection moiety can be linked to an antibody using, for example, carbodiimide conjugation (Bauminger and Wilchek, *Meth. Enzymol.* 70:151-159 (1980)).

Antibodies that differentially bind to polypeptides encoded by a fibrostenosis-predisposing allele can be used in immunoassays. Immunoassays include, without limitation, radioimmunoassays, enzyme-linked immunosorbent assays (ELISAs) and immunoassays with fluorescently labeled antibodies, which are well known in the art. Antibodies can also be used to detect the presence or absence of a polypeptide of interest in a cell or tissue using immunohistochemistry or other in situ assays. Furthermore, cells containing a polypeptide of interest either on the surface of the cell or internally can be detected by an antibody using assays such as fluorescence activated cell sorting (FACS). One skilled in the art understands that these and other routine assays can be useful for determining the presence or absence of the gene product of a fibrostenosis-predisposing allele according to a method of the invention.

The methods of the invention optionally include generating a report indicating the presence or absence in a individual of a fibrostenosis-predisposing allele or fibrostenosis-predisposing haplotype. The methods of the invention also optionally include generating a report indicating the presence or absence in the individual of a clinical subtype of Crohn's disease characterized by fibrostenosing disease or the risk that an individual has of having or developing the fibrostenosing subtype of Crohn's disease.

A report can be in a variety of forms, for example, a report can be printed on paper or a report can be an electronic report that is not printed but is transmitted over an electronic medium such as electronic mail or a computer diskette. A report also can be an oral report that indicates the presence or absence in the individual of a fibrostenosis-predisposing allele or a clinical subtype of Crohn's disease characterized by fibrostenosing disease.

The invention also provides a method of optimizing therapy in an individual by determining the presence or absence in the individual of a fibrostenosis-predisposing allele linked to a NOD2/CARD15 locus, diagnosing individuals in which the fibrostenosis-predisposing allele is present as having a fibrostenosing subtype of Crohn's disease, and treating the individual having a fibrostenosing subtype of Crohn's disease based on the diagnosis. Treatment for the fibrostenosing subtype of Crohn's disease currently includes, for example, surgical removal of the affected, strictured part of the bowel. In one embodiment, the presence or absence of a fibrostenosis-predisposing allele is determined in an individual having a known diagnosis of Crohn's disease. In another embodiment, the diagnosis is recorded in the form of a report as described above.

The following examples are intended to illustrate but not limit the present invention.

EXAMPLE I

Selection and Characterization of Study Subjects

This example describes the clinical characterization of how two cohorts of Crohn's disease patients.

A. Selection of Study Subjects

Two cohorts of Crohn's disease patients were consecutively identified from an inflammatory bowel disease referral center (Cedars-Sinai Medical Center Inflammatory Bowel Disease Center). The first cohort of 142 patients, ascertained between 1993-1996 and designated "CD1", was previously described in Vasiliauskas et al., *Gut* 47:487-496 (2000)). The second cohort of 59 patients (Cohort 2) was collected between 1999-2001 and designated "CD2". A cohort of 175 patients with ulcerative colitis was used as an inflammatory bowel disease control group. This study, which was reviewed and approved for human subject participation by the Cedars-Sinai Institutional Review Board, involved the collection of clinical, serologic and genetic data from patients consenting to the study.

A diagnosis of Crohn's disease in the cohort patients was defined by the presence of a combination of established features from at least two of the following categories: 1) clinical—perforating or fistulizing disease, obstructive symptoms secondary to small bowel stenosis or stricture; 2) endoscopic—deep linear or serpiginous ulcerations, discrete ulcers in normal-appearing mucosa, cobblestoning, or discontinuous or asymmetric inflammation; 3) radiographic—segmental disease (skip lesions), small bowel or colon strictures, stenosis, or fistula, and; 4) histopathologic-submucosal or transmural inflammation, multiple granulomas, marked focal cryptitis or focal chronic inflammatory infiltration within and between biopsies, or skip lesions including rectal sparing in the absence of local therapy.

To identify clinical features and immunological traits associated with allelic variants of the NOD2/CARD15 gene, the study was designed to analyze two consecutively ascertained cohorts of patients with Crohn's disease. The first cohort was used to explore the relationship of NOD2/CARD15 alleles with an array of clinical and serologic variables, thereby generating hypotheses. The second cohort was then used to confirm the specific hypotheses generated from analysis of the first cohort. To minimize type I error and maximize statistical power, the significance of the associations in the first cohort were permitted to be less stringent ($p<0.1$) than in the second cohort ($p<0.05$). By avoiding a highly stringent correction for the number of variables examined in the first cohort, there was an increased ability to identify specific associations between NOD2/CARD15 allele variants and clinical variables.

B. Clinical Characterization of Study Subjects

Patients with Crohn's disease were characterized as having fibrostenosing disease, internal-perforating disease, perianal fistulizing disease or ulcerative colitis (UC)-like disease based on previously described criteria (Gasche et al., *Inflam-* matory Bowel Diseases 6:8-15 (2000); Vasiliauskas et al., Gut 47:487-496 (2000); Vasiliauskas et al., Gastroenterology 110:1810-1819 (1996); and Greenstein et al., Gut 29:588-592 (1988)). According to well established criteria, fibrostenosing disease was defined by documented persistent intestinal obstruction or an intestinal resection for an intestinal obstruction. Internal perforating disease was defined as current or previous evidence of entero-enteric or entero-vesicular fistulae, intraabdominal abscesses, or small bowel perforation. Perianal perforating disease was defined by current or previous evidence of either perianal fistulae or abscesses or rectovaginal fistula. UC-like disease was defined by current or previous evidence of left-sided colonic involvement, symptoms of bleeding or urgency, and crypt abscesses on colonic biopsies as previously described. Disease location was classified as small bowel, colon, or both based on one or more endoscopic, radiologic or pathologic studies. A panel of inflammatory bowel disease physicians unaware of the results of serologic and genetic testing reached a consensus on phenotype based on the clinical data.

Serum ANCA expression and ANCA subtype characterization were performed by fixed neutrophil enzyme-linked immunosorbent assay (ELISA) as previously described (Saxon et al., J. Allergy Clin. Immunol. 86:202-210 (1990)). Briefly, human peripheral blood neutrophils fixed with methanol were reacted with control and coded sera at a 1:100 dilution. Anti-human immunoglobulin G (IgG) (chain-specific) antibody (Jackson Immunoresearch Labs, Inc.; West Grove, Pa.) conjugated to alkaline phosphatase was added to label neutrophil-bound antibody, and a calorimetric reaction was performed. Levels were determined relative to a standard consisting of pooled sera obtained from well-characterized pANCA+ UC patients. Results were expressed as ELISA units (EU) per milliliter. ANCA+ sera were further subtyped via indirect immunofluorescent staining to determine the ANCA neutrophil binding pattern, as previously described (Saxon et al., supra, 1990). Sera showing the characteristic perinuclear highlighting and losing the characteristic staining pattern when treated with deoxyribonuclease were termed pANCA+ (Vidrich et al., J. Clin. Immunol. 15:293-299 (1995)). For the purposes of this study, patients were considered pANCA+ if they were both positive for ANCA by ELISA and lost perinuclear immunofluorescence staining with deoxyribonuclease treatment.

Sera were analyzed for ASCA expression in a blinded fashion by using a fixed ELISA assay (Vasiliauskas et al., Gut 47:487-496 (2000); and Vermeire et al., Gastroenterology 120:827-833 (2001)). Two patients in the second cohort did not undergo ASCA testing. High-binding polystyrene microtiter plates were coated with purified phosphopeptidomannans extracted from yeast S. uvarum, a subspecies of S. cerevisiae. Coded patient sera were diluted and added to the wells, followed by an enzyme-linked colorimetric reaction. Color development was proportional to concentrations of ASCA antibody present in the sera. Levels were determined and results expressed as EU per milliliter, relative to a standard, which was derived from a pool of patient sera with well-characterized Crohn's disease found to have reactivity to this antigen. Sera showing ASCA IgG reactivity of >40 EU/mL or IgA reactivity of >20 EU/mL were termed ASCA+. Serological assays were performed at Cedars-Sinai Medical Center and Prometheus Laboratories (San Diego, Calif.) using substantially identical methodology. The clinical characteristics of the two Crohn's disease cohorts are shown in Table 1.

TABLE 1

Clinical Characteristics of Two Crohn's Disease Cohorts

| Clinical characteristics | CD1 n = 142 | CD2 n = 59 | p |
|---|---|---|---|
| Gender (M/F) | 79/63 | 33/26 | 0.969 |
| Age at onset | 22 (4-67) | 22 (2-58) | 0.6621 |
| Ethnicity (Jew/Non-Jew) | 60/82 | 23/36 | 0.668 |
| Disease location (%) | | | |
| SB only | 19.0 | 26.4 | 0.496 |
| Colon only | 20.4 | 20.8 | |
| SB and Colon | 60.6 | 52.8 | |
| Perianal perforating (%) | 35.9 | 28.8 | 0.332 |
| Internal perforating (%) | 47.2 | 23.7 | 0.002 |
| Fibrostenosing disease (%) | 59.9 | 30.5 | 0.001 |
| UC-like (%) | 39.4 | 22.0 | 0.018 |
| pANCA-positive (%) | 19.7 | 12.5 | 0.295 |
| ASCA-positive* (%) | 57.0 | 38.6 | 0.019 |

EXAMPLE II

Patients with Crohn's Disease Have an Increased Frequency of Rare Allelic Variants of NOD2/CARD15

This example describes the association of a "2" allele at SNP 8, SNP 12, or SNP 13 within the NOD2/CARD15 locus (rare allelic variants of NOD2/CARD15) with Crohn's disease in a North American population.

In order to determine whether the North American Crohn's disease patient populations in Cohorts 1 and 2 expressed allelic variants of NOD2/CARD15, Cohort 1 (hypothesis-generating) and Cohort 2 (hypothesis-confirming) were genotyped for the rare allelic variant of SNP 8 (R675W), SNP 12 (G881R) and SNP 13 (3020insC). A cohort of ulcerative colitis patients was used for comparison.

Genotyping was performed using a genotyping assay employing 5'-exonuclease technology, the TaqMan MGB™ assay (PE Biosystems; Foster City, Calif.). Primers were designed using the software PrimerExpress 1.5™ (PE Biosystems) and sequence information found in dbSNP for NOD2/CARD15 SNP 5, 8, 12, and 13. The MGB™ design adds a "minor groove binder" to the 3' end of the TaqMan™ probes, thereby increasing the binding temperature of the probe and enabling the use of shorter probes than in conventional TaqMan™ assays (Kutyavin et al., Nucleic Acids Res. 25:3718-3723 (1997)). This has the effect of increasing the discrimination between the alleles in the assay (Kutyavin et al., Nucleic Acids Res. 28:655-661 (2000)). Assays were performed following the manufacturer's recommendations (PE Biosystems bulletin 4317594) in an ABI 7906 instrument. Genotyping was performed blinded to clinical status of the subjects. Primers and probes used in the genotyping assay are shown in Tables 2 and 3.

TABLE 2

Primers Used in Taqman MGB ™ Assay for SNPs 5, 8, 12 and 13

| SNP | Forward Primer | Reverse Primer | SEQ ID NO |
|---|---|---|---|
| 5 | 5'GGTGGCTGGGC TCTTCT 3' | 5'CTCGCTTCCTCAGTACCTAT GATG 3' | for 37 rev 38 |

TABLE 2-continued

Primers Used in Taqman MGB ™ Assay for SNPs
5, 8, 12 and 13

| SNP Primer | Forward Primer | Reverse Primer | SEQ ID NO |
|---|---|---|---|
| 8 | 5'CTGGCTGAGTG CCAGACATCT 3' | 5'GGCGGGATGGAGTGGAA 3' | for 39 rev 40 |
| 12 | 5'CCACCTCAAGC TCTGGTGATC 3' | 5'GTTGACTCTTTTGGCCTTTT CAG 3' | for 41 rev 42 |
| 13 | 5'CCTTACCAGAC TTCCAGGATGGT 3' | 5'TGTCCAATAACTGCATCACC TACCT 3' | for 43 rev 44 |

TABLE 3

TAQMAN PROBES

| Allele detected | Probe sequence | Seq ID NO |
|---|---|---|
| SNP5 wild type allele ("1") | 6FAM-CATGGCTGGACCC-MGBNFQ | 45 |
| SNP5 variant allele ("2") | TET-CATGGCTGGATCC-MGBNFQ | 46 |
| SNP8 wild type allele ("1") | 6FAM-TGCTCCGGCGCCA-MGBNFQ | 47 |
| SNP8 variant allele ("2") | TET-CTGCTCTGGCGCCA-MGBNFQ | 48 |
| SNP12 wild type allele ("1") | 6FAM-CTCTGTTGCCCCAGAA-MGBNFQ | 49 |
| SNP12 variant allele ("2") | TET-CTCTGTTGCGCCAGA-MGBNFQ | 50 |
| SNP 13 wild type allele ("1") | TET-CTTTCAAGGGCCTGC-MGBNFQ | 51 |
| SNP13 variant allele ("2") | 6FAM-CCTTTCAAGGGGCCT-MGBNFQ | 52 |
| JW1 wild type allele | 6FAM-AAGACTCGAGTGTCCT-MGBNFQ | 53 |
| JW1 variant | VIC-AGACTCAAGTGTCCTC-MGBNFQ | 54 |

As shown in Table 4, each of three rare allelic variants of NOD2/CARD15 (a "2" allele at SNP 8, SNP 12, or SNP 13) was significantly more frequent in patients with Crohn's disease compared with ulcerative colitis. In addition, as can be seen in Table 4, the frequency of each of the NOD2/CARD15 rare allelic variants was similar in each cohort of Crohn's disease patients, supporting the combined use of the two cohorts. The overall frequency of any of the three NOD2/CARD15 rare allelic variants was 35% in Crohn's disease patients compared with 11% in ulcerative colitis patients ($p=0.001$).

Within the combined Crohn's disease cohort, the frequency of homozygotes with a "2" allele at SNP 13 (3020insC) and compound rare allelic heterozygotes was 1% and 4%, respectively, while none of the ulcerative colitis patients had such a genotype. These results demonstrate that rare allelic variants of NOD2/CARD15 are associated with Crohn's disease across diverse geographic and ethnically-defined patient populations.

TABLE 4

Frequency of NOD2/CARD15 Rare Allelic Variants in CD and UC Patient Populations

| Allelic variants | UC (n = 175) | CD1 (n = 142) | CD2 (n = 59) | Combined CD1 and CD2 (n = 201) | p (UC vs. Combined CD) |
|---|---|---|---|---|---|
| R675W (SNP 8 "2" allele) | 5.7% | 16.9% | 15.3% | 16.4% | 0.001 |
| G881R (SNP 12 "2" allele) | 1.7% | 12.0% | 10.2% | 11.4% | 0.0001 |
| 3020insC (SNP 13 "2" allele) | 3.4% | 11.3% | 11.9% | 11.4% | 0.004 |
| Carriage of any allelic variant | 10.9% | 36.6% | 32.2% | 35.3% | 0.001 |

EXAMPLE III

Rare Variant Alleles in the NOD2/CARD15 Locus are Associated with the Fibrostenosing Subtype of Crohn's Disease in Cohort 1

This example demonstrates that a "2" allele at SNP 8, SNP 12, or SNP 13 is significantly associated with fibrostenosing disease in Cohort 1.

Patients with Crohn's disease express diverse clinical phenotypes that can be due to differences in underlying genetic factors. In order to determine whether rare variant alleles at the NOD2/CARD15 locus were associated with specific Crohn's disease-related clinical phenotypes or disease-related serum immune markers, univariate analysis was performed. The univariate analysis evaluated the association between NOD2/CARD15 allelic variants at SNP 8, SNP 12, or SNP 13 and predefined clinical characteristics, including age of onset, disease location, and disease phenotype (fibrostenosing disease, internal-perforating disease, perianal fistulizing disease or ulcerative colitis-like disease). The association between NOD2/CARD15 allelic variants and expression of the serum immune markers ASCA and pANCA was also tested.

As shown in Table 5, univariate analysis indicated that a "2" allele at SNP 8, SNP 12, or SNP 13 of the NOD2/CARD15 locus was significantly associated with fibrostenosing disease in Cohort 1 ($p=0.049$) for the three allelic variants combined. A positive association at a less stringent significance level ($p<0.1$) was also observed with small bowel involvement and younger age of onset, and a negative association was observed with UC-like disease in this cohort. With respect to serologic markers, patients with the "2" allele at SNP 13 were more likely to express ASCA ($p=0.053$). These results demonstrate that a "2" allele at SNP 8, SNP 12, or SNP 13 is significantly associated with fibrostenosing disease in Cohort 1.

Statistical analysis was performed using SAS computer software (Version 6.10; SAS Institute, Inc.; Cary, N.C.). Quantitative variables were described as medians with a range. Nonparametric statistical tests were used to test differences in quantitative variables between two groups. A Chi-square test or Fisher's exact test (when the expected number was less than 5) was used to evaluate associations between carriers and non-carriers of the rare alleles or between genotypes and categorical variables, such as type of IBD, disease location, disease behavior, and antibody positivity. In addition, a Mantel Haenszel stratified association test was performed for all genotype and phenotype associations by controlling for potential confounding effect due to ethnic variation. This stratified association test was also used to evaluate whether the small bowel involvement and fibrostenosing disease were independently associated with NOD2/CARD15 variants (see Example IX below).

TABLE 5

Relationship of NOD2/CARD15 Rare Variant Alleles and Clinical Phenotypes of Crohn's Disease in Cohort 1

| Clinical phenotypes | | n | Qualitative Trait % NOD2 variant carriers | | | |
|---|---|---|---|---|---|---|
| | | | R675W (SNP 8) | G881R (SNP 12) | 3020insC (SNP 13) | Carriage of any allelic variant |
| Small bowel involvement | yes | 113 | 19.47% | 11.50% | 14.16% | 40.71% |
| | no | 29 | 6.90% | 13.79% | 0.00% | 20.69% |
| p value | | | 0.081 | 0.494 | 0.04 | 0.063 |
| Perianal perforating | yes | 51 | 11.76% | 11.76% | 13.73% | 35.29% |
| | no | 91 | 19.78% | 12.09% | 9.89% | 37.36% |
| p value | | | 0.248 | 0.839 | 0.547 | 0.747 |
| Internal perforating | yes | 67 | 13.43% | 16.42% | 11.94% | 37.31% |
| | no | 75 | 20.00% | 8.00% | 10.67% | 36.00% |
| p value | | | 0.346 | 0.178 | 0.91 | 0.96 |
| Fibro-stenosing | yes | 85 | 18.82% | 14.12% | 15.29% | 43.53% |
| | no | 57 | 14.04% | 8.77% | 5.26% | 26.32% |
| p value | | | 0.389 | 0.458 | 0.084 | 0.049 |
| UC-like | yes | 56 | 17.86% | 10.71% | 5.36% | 30.36% |
| | no | 86 | 16.28% | 12.79% | 15.12% | 40.70% |
| p value | | | 0.822 | 0.736 | 0.076 | 0.22 |
| pANCA positive | yes | 28 | 17.86% | 14.29% | 7.14% | 32.14% |
| | no | 114 | 16.67% | 11.40% | 12.28% | 37.72% |
| p value | | | 0.82 | 0.793 | 0.394 | 0.529 |
| ASCA positive | yes | 81 | 18.52% | 9.88% | 16.05% | 38.27% |
| | no | 61 | 14.75% | 14.75% | 4.92% | 34.43% |
| p value | | | 0.467 | 0.234 | 0.053 | 0.744 |

| | | Quantitative Trait median (range) | | | |
|---|---|---|---|---|---|
| | | R675W (SNP 8) | G881R (SNP 12) | 3020insC (SNP 13) | Carriage of any allelic variant |
| Age of onset carrier of NOD2 variant | yes | 22 (6-67) | 22 (4-62) | 19 (10-50) | 20 (4-67) |
| | no | 22 (4-63) | 22 (4-67) | 22 (4-67) | 22 (4-63) |
| p | | 0.715 | 0.937 | 0.074 | 0.238 |

EXAMPLE IV

Rare Variant Alleles in the NOD2/CARD15 Locus are Associated with the Fibrostenosing Subtype of Crohn's Disease in Cohort 2

This example demonstrates that a "2" allele at SNP 8, SNP 12, or SNP 13 of the NOD2/CARD15 locus is significantly associated with fibrostenosing disease in Cohort 2.

The results obtained with Cohort 1 in Example III indicated that NOD2/CARD15 rare variant alleles were positively associated with fibrostenosing Crohn's disease, small bowel involvement, ASCA positivity, and younger age of onset, and negatively associated with UC-like disease (see Table 5). These hypotheses were further tested using Cohort 2; the results are shown in Table 6. As with Cohort 1, Cohort 2 demonstrated a significant association between a "2" allele at SNP 8, SNP 12, or SNP 13 of the NOD2/CARD15 locus and fibrostenosing disease (p=0.002, with Bonferroni correction p=0.01; see Table 6). These results indicate that a "2" allele at SNP 8, SNP 12, or SNP 13 of the NOD2/CARD15 locus is significantly associated with fibrostenosing disease in Cohort 2.

TABLE 6

Relationship of NOD2/CARD15 Rare Variant Alleles and Clinical Phenotypes of Crohn's Disease in Cohort 2

| Clinical phenotypes | | n | Qualitative Trait % NOD2 variant carriers | | | |
|---|---|---|---|---|---|---|
| | | | R675W (SNP 8) | G881R (SNP 12) | 3020insC (SNP 13) | Carriage of any allelic variant |
| Fibro-stenosing | yes | 18 | 22.22% | 22.22% | 27.78% | 61.11% |
| | no | 41 | 12.20% | 4.88% | 4.88% | 19.51% |
| p | | | 0.315 | 0.048 | 0.018 | 0.002 |
| Small bowel involvement | yes | 42 | 19.05% | 9.52% | 14.29% | 35.71% |
| | no | 17 | 5.88% | 11.76% | 5.88% | 23.53% |
| p | | | 0.22 | 0.828 | 0.288 | 0.354 |
| ASCA positive | yes | 22 | 9.09% | 13.64% | 13.64% | 31.82% |
| | no | 35 | 17.14% | 8.57% | 11.43% | 31.43% |
| p | | | 0.4 | 0.542 | 0.735 | 0.956 |

| | | Quantitative Trait median (range) | | | |
|---|---|---|---|---|---|
| | | R675W (SNP 8) | G881R (SNP 12) | 3020insC (SNP 13) | Carriage of any allelic variant |
| Age of onset carrier of NOD2 variant | yes | 27 (10-58) | 26 (7-33) | 17 (13-35) | 22 (7-58) |
| | no | 19 (2-55) | 20 (2-58) | 24 (2-58) | 22 (2-55) |
| p | | 0.332 | 0.9 | 0.566 | 0.981 |

EXAMPLE V

Rare Variant Alleles in the NOD2/CARD15 Locus are Associated with the Fibrostenosing Subtype of Crohn's Disease in a Combined Cohort Representing Cohorts 1 and 2

This example demonstrates that a "2" allele at SNP 8, SNP 12, or SNP 13 is significantly associated with fibrostenosing disease in a combined cohort representing cohorts 1 and 2.

Figure 2:
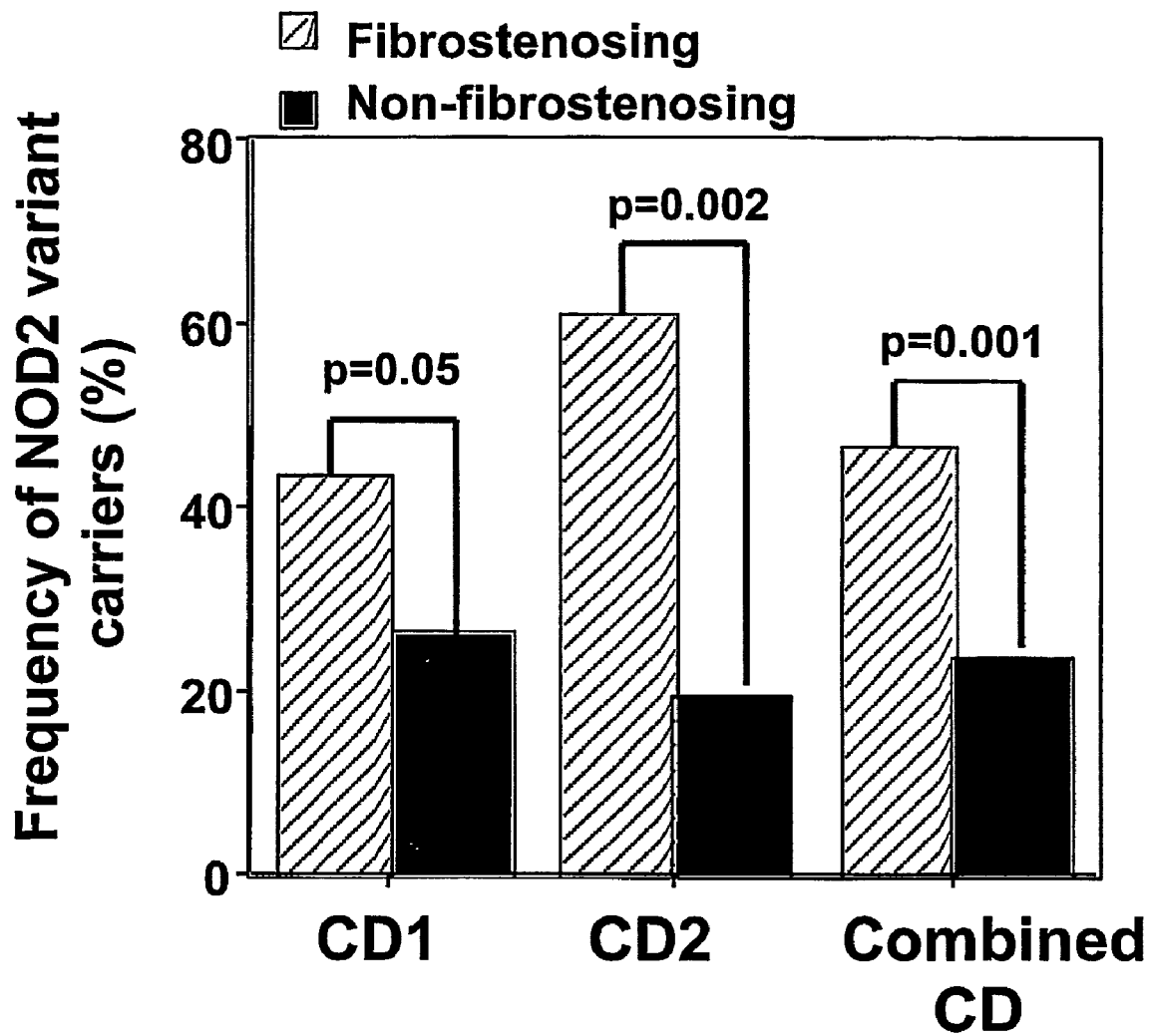
FIG. 2 shows the frequency of NOD2 variant carriers having at least one of the three NOD2/CARD15 rare variant alleles (a "2" allele at SNP 8, SNP 12 or SNP 13) in Cohort 1 ("CD1"), Cohort 2 ("CD2") or a combination of Cohort 1 and Cohort 2 ("Combined CD"). The striped bars indicate Crohn's disease patients with fibrostenosing disease and the solid bars indicate Crohn's disease patients who did not have the fibrostenosing subtype of disease.

As seen in FIG. 2, the association between a "2" allele at SNP 8, SNP 12, or SNP 13 of the NOD2/CARD15 locus (NOD2 variant carrier) and fibrostenosing disease was even more significant (p=0.001) when the two cohorts were analyzed together than when analyzed separately.

The association between a "2" allele at SNP 8, SNP 12, or SNP 13 of the NOD2/CARD15 locus (NOD2 variant carrier) and fibrostenosing disease was observed in both Jewish and non-Jewish individuals. Approximately 46% of Crohn's disease patients with fibrostenosing disease (Jews 52% vs. non-Jews 42%) had at least one of these rare alleles compared with only 23% (Jews 21.6% vs. non-Jews 25%) of Crohn's disease patients without fibrostenosing disease (Odds ratio, 2.8; 95% Confidence interval, 1.56-5.18). Of the three rare variant alleles, the frameshift mutation 3020insC (a "2" allele at SNP 13) demonstrated the greatest association with fibrostenosing disease (47% vs. 17%, p=0.006 for cohorts combined). These results indicate that rare variant alleles in the NOD2/CARD15 locus are associated with the fibrostenosing subtype of Crohn's disease in a combined cohort representing Cohorts 1 and 2.

EXAMPLE VI

Crohn's Disease Patients with Homozygous Mutations or Compound Heterozygous Mutations in NOD2/CARD15

This example describes the increased risk of fibrostenosing disease in Crohn's disease patients carrying homozygous mutations or compound heterozygous mutations in NOD2/CARD15 locus.

Figure 3:
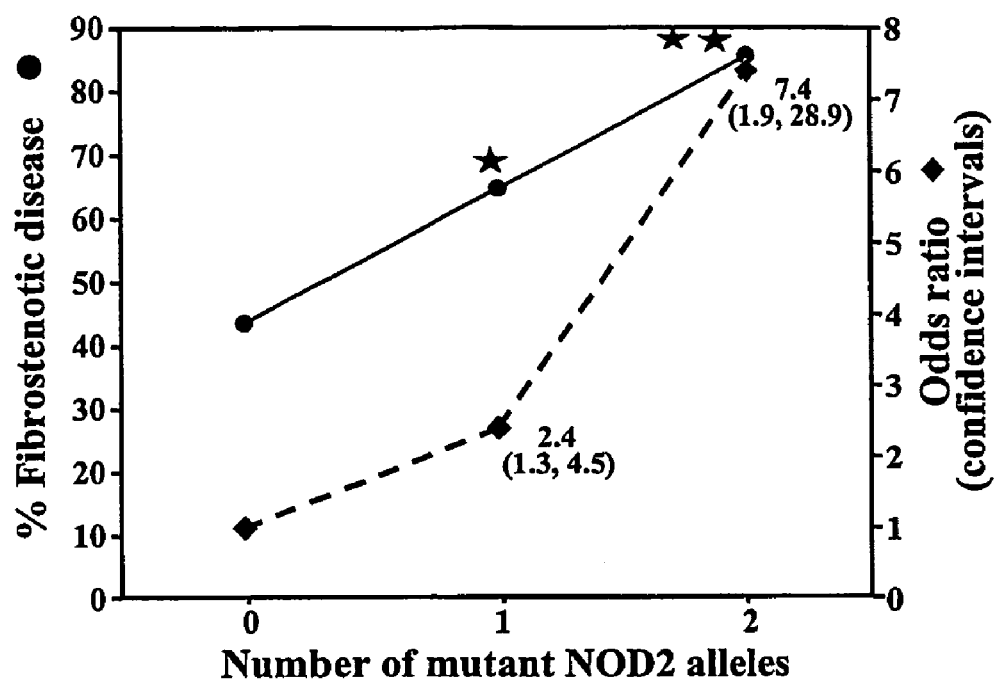
FIG. 3 shows the frequency of fibrostenosing complications in patients relative to the number of NOD2/CARD15 rare variant alleles at SNP 8, SNP 12 or SNP 13. Based on genotyping at SNP 8, SNP 12 and SNP 13, patients were described as carrying 0, 1, or 2 rare variant alleles (x axis, number of mutant NOD2 alleles). The left y axis shows the frequency of fibrostenosing complications as filled circles. The right y axis shows the odds ratio as a filled diamond with 95% confidence intervals in parentheses. The * indicates a p value=0.008 and ** indicates a p value of 0.004 compared with 0 alleles.

As shown in FIG. 3, compared with patients who were not carriers of NOD2/CARD15 mutations at SNP 8, SNP 12 or SNP 13, patients who were carriers of two mutations in NOD2/CARD15 were significantly more likely to have fibrostenosing disease (85% vs. 43%; odds ratio 7.4; 95% confidence interval 1.9-28.9, p=0.004). Patients who were carriers of a single NOD2/CARD15 mutation were also significantly more likely to have fibrostenosing disease when compared with patients who were not carriers of these NOD2/CARD15 mutations (64% vs. 43%; Odds ratio 2.37; 95% Confidence interval 1.26-4.47; p=0.008). These results indicate that Crohn's disease patients with homozygous mutations or compound heterozygous mutations in NOD2/CARD15 have an increased risk of fibrostenosing disease.

EXAMPLE VII

Fibrostenosing Disease Only Compared to Fibrostenosing and Perforating Disease This example describes the association of the "2" allele at SNP 8, SNP 12, or SNP 13 of the NOD2/CARD15 locus in patients with fibrostenosing disease compared to patients with fibrostenosing and perforating disease.

Fibrostenosing and perforating disease often occur in the same patient. Patients with fibrostenosing disease can be characterized as i) having only fibrostenosing disease or ii) having both fibrostenosing and perforating disease. In order to address these phenotypes individually, patients in each of the two cohorts were separated by the presence of fibrostenosing disease with perforating complications (Fib+perf) or without perforating complications (Fib only) and compared with patients with perforating complications without evidence of fibrostenosis (Perf only). The percentage of patients having only fibrostenosing disease that carried a "2" allele at SNP 8, SNP 12, or SNP 13 of the NOD2/CARD15 locus was 48.3%, which was similar to that seen in patients with both fibrostenosing and perforating complications (46.0%; p=0.8). As seen in FIG. 3, when patients with fibrostenosing disease were compared with those patients described as having perforating disease only (perianal or internal), the frequency of the "2" allele at SNP 8, SNP 12 or SNP 13 of the NOD2/CARD15 locus in patients with fibrostenosing disease (with or without perforating complications) was significantly greater than that seen in patients with only perforating complications (46.6% versus 18.6%; p=0.002).

EXAMPLE VIII

Multivariant Analysis of the Combined Patient Cohort

This example demonstrates that fibrostenosing disease is independently associated with a "2" allele at SNP 8, SNP 12, or SNP 13 of the NOD2/CARD15 locus.

For multivariant analysis, all variables with at least borderline significance (p<0.1) in either cohort were tested simultaneously for their association with a "2" allele at SNP 8, SNP 12, or SNP 13 of the NOD2/CARD15 locus by using logistic regression. As shown in Table 7, the clinical phenotype of fibrostenosing disease was significantly associated (p<0.05) with these rare alleles at NOD2/CARD15 locus (OR 2.8; 95% CI, 1.3-6.0). These results confirm that fibrostenosing disease is independently associated with a "2" allele at SNP 8, SNP 12, or SNP 13 of the NOD2/CARD15 locus.

TABLE 7

| Multivariate Analysis in the Combined Cohort for 5 Phenotypic Variables | | | |
|---|---|---|---|
| Clinical phenotypes | OR | 95% CI | P |
| Fibrostenosing disease | 2.8 | 1.3-6.0 | 0.011 |
| Small bowel involvement | 1.3 | 0.5-3.4 | 0.561 |
| UC-like | 0.9 | 0.4-1.7 | 0.658 |
| ASCA positive | 0.7 | 0.3-1.3 | 0.250 |
| Age of onset | 1.0 | 0.9-1.0 | 0.874 |

EXAMPLE IX

Fibrostenosing Disease and Small-Bowel Involvement

This example demonstrates that the association between fibrostenosing disease and a "2" allele at SNP 8, SNP 12, or SNP 13 of the NOD2/CARD15 locus is independent of small-bowel involvement.

Because fibrostenosing disease is more likely to occur in patients with small-bowel involvement, patients were stratified on the basis of small-bowel involvement to analyze whether the association between fibrostenosing disease and NOD2/CARD15 variant alleles was a primary association. Among patients with small-bowel involvement, 26.4% of patients who did not have fibrostenosing disease (n=53) had a "2" allele at SNP 8, SNP 12, or SNP 13, whereas 46.1% of patients who had fibrostenosing disease (n=102) had a "2" allele at SNP 8, SNP 12, or SNP 13 (p=0.017). A similar trend was observed among patients without small-bowel involvement (p=0.05), and the combined analysis conditioning on small-bowel involvement yielded a significance level of 0.009.

After controlling for fibrostenosing disease, small-bowel involvement was not associated with a "2" allele at SNP 8, SNP 12, or SNP 13 of the NOD2/CARD15 locus (p=0.63). This result agrees with the results from logistic regression analysis (see Example VIII) and indicates that the association between fibrostenosing disease and a "2" allele at SNP 8, SNP 12, or SNP 13 of the NOD2/CARD15 locus is independent of small-bowel involvement. These results further indicate that the observed small-bowel association with a "2" allele at SNP 8, SNP 12, or SNP 13 of the NOD2/CARD15 locus is secondary to the presence of fibrostenosing disease.

All journal article, reference, and patent citations provided above, in parentheses or otherwise, whether previously stated or not, are incorporated herein by reference.

Although the invention has been described with reference to the examples above, it should be understood that various modifications can be made without departing from the spirit of the invention. Accordingly, the invention is limited only by the following claims.

We claim:

1. A method of diagnosing or predicting susceptibility to a clinical subtype of Crohn's disease characterized by fibrostenosing disease, said method comprising:
   (a) genotyping an individual for the presence or absence of the SNP 13 allele in the NOD2/CARD15 gene using enzymatic amplification of nucleic acid from said individual, wherein said SNP 13 allele is an insertion of a G at position 248 of SEQ ID NO:5 or an insertion of a C at position 294 of SEQ ID NO:6; and
   (b) indicating that the presence of said SNP 13 allele is diagnostic of or predictive of susceptibility to the clinical subtype of Crohn's disease characterized by fibrostenosing disease.

2. The method of claim 1, wherein NF-kappa B activation by a NOD2/CARD15 polypeptide encoded by said SNP 13 allele is reduced as compared to NF-kappa B activation by a wild-type NOD2/CARD 15 polypeptide.

3. The method of claim 1, wherein said SNP 13 allele is associated with said clinical subtype of Crohn's disease characterized by fibrostenosing disease with an odds ratio of at least 2 and a lower 95% confidence limit greater than 1.

4. The method of claim 1, further comprising generating a report indicating the presence or absence in said individual of said SNP 13 allele.

5. The method of claim 1, further comprising generating a report indicating the presence or absence in said individual of said clinical subtype of Crohn's disease characterized by fibrostenosing disease.

6. The method of claim 1, wherein said amplification is polymerase chain reaction amplification.

7. The method of claim 6, wherein said polymerase chain reaction amplification is performed using one or more fluorescently labeled probes.

8. The method of claim 6, wherein said polymerase chain reaction amplification is performed using one or more probes comprising a DNA minor groove binder.

9. A method of optimizing therapy in an individual, said method comprising:
   (a) genotyping an individual for the presence or absence of the SNP 13 allele in the NOD2/CARD 15 gene using enzymatic amplification of nucleic acid from said individual, wherein said SNP 13 allele is an insertion of a G at position 248 of SEQ ID NO:5 or an insertion of a C at position 294 of SEQ ID NO:6;
   (b) diagnosing individuals in which said SNP 13 allele is present as having a fibrostenosing subtype of Crohn's disease; and
   (c) treating said individual having a fibrostenosing subtype of Crohn's disease based on said diagnosis.

10. The method of claim 9, wherein said SNP 13 allele is associated with said clinical subtype of Crohn's disease characterized by fibrostenosing disease with an odds ratio of at least 2 and a lower 95% confidence limit greater than 1.

11. The method of claim 9, further comprising generating a report indicating the presence or absence in said individual of said SNP 13 allele.

12. The method of claim 9, further comprising generating a report indicating the presence or absence in said individual of said clinical subtype of Crohn's disease characterized by fibrostenosing disease.

13. The method of claim 9, wherein said amplification is polymerase chain reaction amplification.

14. The method of claim 13, wherein said polymerase chain reaction amplification is performed using one or more fluorescently labeled probes.

15. The method of claim 13, wherein said polymerase chain reaction amplification is performed using one or more probes comprising a DNA minor groove binder.

* * * * *

SEQUENCE LISTING

<160> NUMBER OF SEQ ID NOS: 67

<210> SEQ ID NO 1
<211> LENGTH: 494
<212> TYPE: DNA
<213> ORGANISM: Homo sapiens

<400> SEQUENCE: 1

```
accttcagat cacagcagcc ttcctggcag ggctgttgtc ccgggagcac tggggcctgc      60
tggctgagtg ccagacatct gagaaggccc tgctccggcg ccaggcctgt gcccgctggt     120
gtctggcccg cagcctccgc aagcacttcc actccatccc gccagctgca ccgggtgagg     180
ccaagagcgt gcatgccatg cccggttca tctggctcat ccggagcctg tacgagatgc      240
aggaggagcg gctggctcgg aaggctgcac gtggcctgaa tgttgggcac ctcaagttga     300
cattttgcag tgtgggcccc actgagtgtg ctgccctggc ctttgtgctg cagcacctcc     360
ggcggcccgt ggccctgcag ctggactaca actctgtggg tgacattggc ctggagcagc     420
tgctgccttg ccttggtgtc tgcaaggctc tgtagtgagt gttactgggc attgctgttc     480
aggtatgggg gagc                                                      494
```

<210> SEQ ID NO 2
<211> LENGTH: 494
<212> TYPE: DNA
<213> ORGANISM: Homo sapiens

<400> SEQUENCE: 2

```
gctcccccat acctgaacag caatgcccag taacactcac tacagagcct tgcagacacc      60
aaggcaaggc agcagctgct ccaggccaat gtcacccaca gagttgtagt ccagctgcag     120
ggccacgggc cgccggaggt gctgcagcac aaaggccagg gcagcacact cagtggggcc     180
cacactgcaa aatgtcaact tgaggtgccc aacattcagg ccacgtgcag ccttccgagc     240
cagccgctcc tcctgcatct cgtacaggct ccggatgagc cagatgaacc cgggcatggc     300
atgcacgctc ttggcctcac ccggtgcagc tggcgggatg gagtggaagt gcttgcggag     360
gctgcgggcc agacaccagc gggcacaggc ctggcgccgg agcagggcct tctcagatgt     420
ctggcactca gccagcaggc cccagtgctc ccgggacaac agccctgcca ggaaggctgc     480
tgtgatctga aggt                                                      494
```

<210> SEQ ID NO 3
<211> LENGTH: 540
<212> TYPE: DNA
<213> ORGANISM: Homo sapiens

<400> SEQUENCE: 3

```
atcaaaaccc tgagaggaca agggacattt ccaagtcacc cagaaagact cgagtgtcct      60
ctcttgaaat ccaatggtct tttttcctta ctccattgcc taacattgtg gggtagaaat     120
```

| aaagttcaaa gaccttcaga actggcccca gctcctccct cttcacctga tctccccaag | 180 |
| aaaactgcag gatagactct gaagcttacc tgagccacct caagtctggt gatcaccca | 240 |
| aggcttcagc cagggcctgg gccccctcgt cacccactct gttgcccag aatctgaaaa | 300 |
| ggccaaaaga gtcaacagac agtgtcagtg agtacctgat atgtgttcta gacatgaact | 360 |
| aacagtcctc ctccctctgc agtcccagcc agaggggcag gaccactcaa tcccagagtg | 420 |
| gcctcactgg ggctcctggt cccagcaaag tggacctgcc tccatctttt gggtgggatg | 480 |
| gccaaactta acccaagagt tttcagtggc tttacattac agacttagag aatagtagag | 540 |

<210> SEQ ID NO 4
<211> LENGTH: 540
<212> TYPE: DNA
<213> ORGANISM: Homo sapiens

<400> SEQUENCE: 4

| ctctactatt ctctaagtct gtaatgtaaa gccactgaaa actcttgggt taagtttggc | 60 |
| catcccaccc aaaagatgga ggcaggtcca ctttgctggg accaggagcc ccagtgaggc | 120 |
| cactctggga ttgagtggtc ctgcccctct ggctgggact gcagaggag gaggactgtt | 180 |
| agttcatgtc tagaacacat atcaggtact cactgacact gtctgttgac tcttttggcc | 240 |
| ttttcagatt ctggggcaac agagtgggtg acgaggggc caggccctg gctgaagcct | 300 |
| tgggtgatca ccagagcttg aggtggctca gtaagcttc agagtctatc ctgcagtttt | 360 |
| cttggggaga tcaggtgaag agggaggagc tggggccagt tctgaaggtc tttgaactttt | 420 |
| atttctaccc cacaatgtta ggcaatggag taaggaaaaa agaccattgg atttcaagag | 480 |
| aggacactcg agtctttctg ggtgacttgg aaatgtccct tgtcctctca gggttttgat | 540 |

<210> SEQ ID NO 5
<211> LENGTH: 541
<212> TYPE: DNA
<213> ORGANISM: Homo sapiens

<400> SEQUENCE: 5

| tttaaaaatg aaatcattgc tccctactta aagaggtaaa gacttctttc ttagacagag | 60 |
| aatcagatcc ttcacatgca gaatcattct cactgaatgt cagaatcaga agggatcctc | 120 |
| aaaattctgc cattcctctc tcccgtcacc ccatttttaca gatagaaaaa ctgaggttcg | 180 |
| gagagctaaa acaggcctgc ccaggggcct taccagactt ccaggatggt gtcattcctt | 240 |
| tcaaggggcc tgcaggaggg cttctgcccc taggtaggtg atgcagttat tggacaacct | 300 |
| ggaaaagaag atacaatggt gagcttcaag gattcttggt tttcctcttg aaactgtcca | 360 |
| gttaaagaga ctgcaggagt tagccagtct actgaagccc acctgtccct tagacacatc | 420 |
| ctgctcatgt ctgagattcc caatgagctc atcaacaaag gctcagtacc atcagtgaaa | 480 |
| tgtaaccgtc tctcttccat tcactagatg agtttatcaa attaagtagc cactcccta | 540 |
| g | 541 |

<210> SEQ ID NO 6
<211> LENGTH: 541
<212> TYPE: DNA
<213> ORGANISM: Homo sapiens

<400> SEQUENCE: 6

| ctaagggagt ggctacttaa tttgataaac tcatctagtg aatggaagag agacggttac | 60 |
| atttcactga tggtactgag cctttgttga tgagctcatt gggaatctca gacatgagca | 120 |

| | |
|---|---|
| ggatgtgtct aagggacagg tgggcttcag tagactggct aactcctgca gtctctttaa | 180 |
| ctggacagtt tcaagaggaa accaagaat ccttgaagct caccattgta tcttcttttc | 240 |
| caggttgtcc aataactgca tcacctacct aggggcagaa gccctcctgc aggcccttg | 300 |
| aaaggaatga caccatcctg gaagtctggt aaggcccctg ggcaggcctg ttttagctct | 360 |
| ccgaacctca gttttttctat ctgtaaaatg gggtgacggg agagaggaat ggcagaattt | 420 |
| tgaggatccc ttctgattct gacattcagt gagaatgatt ctgcatgtga aggatctgat | 480 |
| tctctgtcta agaaagaagt ctttacctct ttaagtaggg agcaatgatt tcattttttaa | 540 |
| a | 541 |

<210> SEQ ID NO 7
<211> LENGTH: 540
<212> TYPE: DNA
<213> ORGANISM: Homo sapiens

<400> SEQUENCE: 7

| | |
|---|---|
| aacagcagtg ctcaaagagt agagtccgca cagagagtgg tttggccatg cactgcagct | 60 |
| gccggcagct gaatgggaag acaaagagaa attcctggaa gtcttgccct gcagcccaca | 120 |
| gcaagtgcag ccgctgcagg agcgtgctct tgccactgcc cgcctcaccc accaccagca | 180 |
| cagtgtccgc atcgtcattg aggtggccag gggtgctgaa gagctcctcc aggcccaggg | 240 |
| tggctgggct cttctgcggg ggtccagcca tgcccacatc tgcccagacc tccaggacat | 300 |
| tctctgtgta tatgtcctcc aggcagagcg tctctgctcc atcataggta ctgaggaagc | 360 |
| gagactgagc agacaccgtg gtcctcagct tggccatata cttcttgcat gtggcagctg | 420 |
| gaaggcagaa gaagaggcag atgaaggtgg caccatggtg aagacgggac ctaaccagac | 480 |
| aatgggctgc tgcgggggac gctgacataa ctgaagggat aggagagcca gcgggcgccc | 540 |

<210> SEQ ID NO 8
<211> LENGTH: 540
<212> TYPE: DNA
<213> ORGANISM: Homo sapiens

<400> SEQUENCE: 8

| | |
|---|---|
| gggcgcccgc tggctctcct atcccttcag ttatgtcagc gtccccgca gcagcccatt | 60 |
| gtctggttag gtcccgtctt caccatggtg ccaccttcat ctgcctcttc ttctgccttc | 120 |
| cagctgccac atgcaagaag tatatggcca agctgaggac cacggtgtct gctcagtctc | 180 |
| gcttcctcag tacctatgat ggagcagaga cgctctgcct ggaggacata tacacagaga | 240 |
| atgtcctgga ggtctgggca gatgtgggca tggctggacc cccgcagaag agcccagcca | 300 |
| ccctgggcct ggaggagctc ttcagcaccc ctggccacct caatgacgat gcggacactg | 360 |
| tgctggtggt gggtgaggcg ggcagtggca agagcacgct cctgcagcgg ctgcacttgc | 420 |
| tgtgggctgc agggcaagac ttccaggaat ttctctttgt cttcccattc agctgccggc | 480 |
| agctgcagtg catggccaaa ccactctctg tgcggactct actctttgag cactgctgtt | 540 |

<210> SEQ ID NO 9
<211> LENGTH: 520
<212> TYPE: DNA
<213> ORGANISM: Homo sapeins

<400> SEQUENCE: 9

| | |
|---|---|
| gcactgggca cccactacca atggattgga attggtcctt aagataaaat gtacctgatc | 60 |

```
cagcccaata tcttcaattt acagatactg tatcaaaacc ctgagaggac aagggacatt    120
tccaagtcac ccagaaagac tcgagtgtcc tctcttgaaa tccaatggtc ttttttcctt    180
actccattgc ctaacattgt ggggtagaaa taaagttcaa agaccttcag aactggcccc    240
agctcctccc tcttcacctg atctccccaa gaaaactgca ggatagactc tgaagcttac    300
ctgagccacc tcaagctctg gtgatcaccc aaggcttcag ccagggcctg ggccccctcg    360
tcacccactc tgttgcccca gaatctgaaa aggccaaaag agtcaacaga cagtgtcagt    420
gagtacctga tatgtgttct agacatgaac taacagtcct cctccctctg cagtcccagc    480
cagaggggca ggaccactca atcccagagt ggcctcactg                          520
```

<210> SEQ ID NO 10
<211> LENGTH: 520
<212> TYPE: DNA
<213> ORGANISM: Homo sapiens

<400> SEQUENCE: 10

```
cagtgaggcc actctgggat tgagtggtcc tgcccctctg gctgggactg cagagggagg     60
aggactgtta gttcatgtct agaacacata tcaggtactc actgacactg tctgttgact    120
cttttggcct tttcagattc tggggcaaca gagtgggtga cgaggggggcc caggccctgg    180 ctgaagcctt gggtgatcac cagagcttga ggtggctcag gtaagcttca gagtctatcc    240
tgcagttttc ttggggagat caggtgaaga gggaggagct ggggccagtt ctgaaggtct    300
ttgaacttta tttctacccc acaatgttag gcaatggagt aaggaaaaaa gaccattgga    360
tttcaagaga ggacactcga gtctttctgg gtgacttgga aatgtcccct gtcctctcag    420
ggttttgata cagtatctgt aaattgaaga tattgggctg gatcaggtac attttatctt    480
aaggaccaat tccaatccat tggtagtggg tgcccagtgc                          520
```

<210> SEQ ID NO 11
<211> LENGTH: 535
<212> TYPE: DNA
<213> ORGANISM: Homo sapiens

<400> SEQUENCE: 11

```
tcactaacca gctcaggaag ctcaccagct tgggaagtta atcattatgt ctagcttcag     60
tttctcctgc ttcagtttaa attgggaaag agagagaaaa aatattcact cattatctgt    120
ttcctaaaat tgtccttaac atccttcctc ttactccttt attacctggt cgggcttccc    180
ctcttcaggc gaaatctgtc agtctatctg cattgccttt tgatctctac ttcagttact    240
acaacttcaa agacaccatt gtcctcccca aggtgaggcc catgtagaga aaggatcact    300
tccttgctga aagagagggt caaggggcga cccacgtggg ccctccctga aacccaggcc    360
caggcctgag cctggacacc tccttccttc ctgagaccac agccagcccg gtttctctgg    420 gccaagagc aaatgctttg cttaagtgct gaaatccag cccactgacc ccttgcagac     480
aggagaggag gggaagccca gggaagctca acttcccaag tgtcctgagt ctctg         535
```

<210> SEQ ID NO 12
<211> LENGTH: 496
<212> TYPE: DNA
<213> ORGANISM: Homo sapiens

<400> SEQUENCE: 12

```
aatcattatg tctagcttca gtttctcctg cttcagttta aattgggaaa gagagagaaa     60
aaatattcac tcattatctg tttcctaaaa ttgtccttaa catccttcct cttactccett    120
```

```
tattacctgg tcgggcttcc cctcttcagg cgaaatctgt cagtctatct gcattgcctt    180
ttgatctcta cttcagttac tacmacttca aagacaccat tgtcctcccc aaggtgaggs    240
ccatgtagag aaaggatcac ttccttgctg aaagagaggg tcaaggggtg acccacgtgg    300
gccctccctg aaacccaggc ccaggcctga gcctggacac ctccttcctt cctgagacca    360
cagccagccc ggtttctctg gggccaagag caaatgcttt gcttaagtgc tgaaatctca    420
gcccactgac cccttgcmga caggagagga ggggaagccc agggaagctc aacttcccaa    480
gtgtcctgag tctctg                                                    496

<210> SEQ ID NO 13
<211> LENGTH: 488
<212> TYPE: DNA
<213> ORGANISM: Homo sapiens
<220> FEATURE:
<221> NAME/KEY: misc_feature
<222> LOCATION: 434
<223> OTHER INFORMATION: n = A,T,C or G

<400> SEQUENCE: 13
tgtctagctt cagtttctcc tgcttcagtt taaattggga agagagaga aaaatattc     60 actcattatc tgtttcctaa aattgtcctt aacatccttc ctcttactcc tttattacct   120
ggtcgggctt cccctcttca ggcgaaatct gtcagtctat ctgcattgcc ttttgatctc   180
tacttcagtt actacaactt caaagacacc attgtcctcc caaggtgag gcccatgtag   240 agaaaggatc acttccttgc tgaaagagag ggtcaagggg tgacccacgt gggccctccc   300
tgaaacccag gcccaggcct gagcctggac acctccttcc ttcctgagac cacagccagc   360
ccggtttctc tggggccaag agcaaatgct ttgcttaagt gctgaaatct cagcccactg   420
amcccttgca dacnggagag gagggaagc ccagggaagc tcaacttccc aagtgtcctg   480
agtctctg                                                            488

<210> SEQ ID NO 14
<211> LENGTH: 491
<212> TYPE: DNA
<213> ORGANISM: Homo sapiens
<220> FEATURE:
<221> NAME/KEY: misc_feature
<222> LOCATION: 437
<223> OTHER INFORMATION: n = A,T,C or G

<400> SEQUENCE: 14
ttatgtctag cttcagtttc tcctgcttca gtttaaattg ggaaagagag agaaaaaata    60
ttcactcatt atctgtttcc taaaattgtc cttaacatcc ttcctcttac tcctttatta   120
cctggtcggg cttcccctct tcaggcgaaa tctgtcagtc tatctgcatt gccttttgat   180
ctctacttca gttactacaa cttcaaagac accattgtcc tccccaaggt gaggcccatg   240
tagagaaagg atcacttcct tgctgaaaga gagggtcaag gggygaccca cgtgggccct   300
ccctgaaacc caggcccagg cctgagcctg gacacctcct tccttcctga gaccacagcc   360
agcccggttt ctctggggcc aagagcaaat gctttgctta agtgctgaaa tctcagccca   420
ctgacccctt gcagacngga gaggaggga agcccaggga agctcaactt cccaagtgtc   480
ctgagtctct g                                                        491

<210> SEQ ID NO 15
<211> LENGTH: 491
<212> TYPE: DNA
```

<213> ORGANISM: Homo sapiens

<400> SEQUENCE: 15

| | |
|---|---|
| ttatgtctag cttcagtttc tcctgcttca gtttaaattg ggaaagagag agaaaaaata | 60 |
| ttcactcatt atctgtttcc taaaattgtc cttaacatcc ttcctcttac tcctttatta | 120 |
| cctggtcggg cttccctct tcaggcgaaa tctgtcagtc tatctgcatt gccttttgat | 180 |
| ctctacttca gttactacaa cttcaaagac accattgtcc tccccaaggt gaggcccatg | 240 |
| tagagaaagg atcacttcct tgctgaaaga gagggtcaag gggygaccca cgtgggccct | 300 |
| ccctgaaacc caggcccagg cctgagcctg acacctcct tccttcctga ccacagcc | 360 |
| agcccggttt ctctggggcc aagagcaaat gctttgctta agtgctgaaa tctcagccca | 420 |
| ctgaccccctt gcagacagga gaggagggga agcccaggga agctcaactt cccaagtgtc | 480 |
| ctgagtctct g | 491 |

<210> SEQ ID NO 16
<211> LENGTH: 491
<212> TYPE: DNA
<213> ORGANISM: Homo sapiens
<220> FEATURE:
<221> NAME/KEY: misc_feature
<222> LOCATION: 437
<223> OTHER INFORMATION: n = A,T,C or G

<400> SEQUENCE: 16

| | |
|---|---|
| ttatgtctag cttcagtttc tcctgcttca gtttaaattg ggaaagagag agaaaaaata | 60 |
| ttcactcatt atctgtttcc taaaattgtc cttaacatcc ttcctcttac tcctttatta | 120 |
| cctggtcggg cttccctct tcaggcgaaa tctgtcagtc tatctgcatt gccttttgat | 180 |
| ctctacttca gttactacaa cttcaaagac accattgtcc tccccaaggt gaggcccatg | 240 |
| tagagaaagg atcacttcct tgctgaaaga gagggtcaag gggygaccca cgtgggccct | 300 |
| ccctgaaacc caggcccagg cctgagcctg acacctcct tccttcctga ccacagcc | 360 |
| agcccggttt ctctggggcc aagagcaaat gctttgctta agtgctgaaa tctcagccca | 420 |
| ctgaccccctt gcagacngga gaggagggga agcccaggga agctcaactt cccaagtgtc | 480 |
| ctgagtctct g | 491 |

<210> SEQ ID NO 17
<211> LENGTH: 491
<212> TYPE: DNA
<213> ORGANISM: Homo sapiens
<220> FEATURE:
<221> NAME/KEY: misc_feature
<222> LOCATION: 159
<223> OTHER INFORMATION: n = A,T,C or G

<400> SEQUENCE: 17

| | |
|---|---|
| ttatgtctag cttcagtttc tcctgcttca gtttaaattg ggaaagagag agaaaaaata | 60 |
| ttcactcatt atctgtttcc taaaattgtc cttaacatcc ttcctcttac tcctttatta | 120 |
| cctggtcggg cttccctct tcaggcgaaa tctgtcagnc tatctgcatt gccttttgat | 180 |
| ctctacttca gttactacaa cttcaaagac accattgtcc tccccaaggt gaggcccatg | 240 |
| tagagaaagg atcacttcct tgctgaaaga gagggtcaag gggygaccca cgtgggccct | 300 |
| ccctgaaacc caggcccagg cctgagcctg acacctcct tccttcctga ccacagcc | 360 |
| agcccggttt ctctggggcc aagagcaaat gctttgctta agtgctgaaa tctcagccca | 420 |
| ctgaccccctt gcagacagga gaggagggga agcccaggga agctcaactt cccaagtgtc | 480 |

```
ctgagtctct g                                                  491

<210> SEQ ID NO 18
<211> LENGTH: 487
<212> TYPE: DNA
<213> ORGANISM: Homo sapiens
<220> FEATURE:
<221> NAME/KEY: misc_feature
<222> LOCATION: 433
<223> OTHER INFORMATION: n = A,T,C or G

<400> SEQUENCE: 18
gtctagcttc agtttctcct gcttcagttt aaattgggaa agagagagaa aaaatattca    60
ctyattatct gtttcctaaa attgtcctta acatccttcc tcttactcct ttattacctg   120
gtcgggcttc ccctcttcag gcgaaatctg tcagtctatc tgcattgcct tttgatctct   180
acttcagtta ctacaacttc aaagacacca ttgtcctccc caaggtgagg cccatgtaga   240
gaaaggatca cttccttgct gaaagagagg gtcaaggggy acccacgtg ggccctccct    300 gaaacccagg cccaggcctg agcctggaca cctccttcct tcctgagacc acagccagcc   360
cggtttctct ggggccaaga gcaaatgctt tgcttaagtg ctgaaatctc agcccactga   420
ccccttgcag acnggagagg aggggaagcc cagggaagct caacttccca agtgtcctga   480
gtctctg                                                             487

<210> SEQ ID NO 19
<211> LENGTH: 486
<212> TYPE: DNA
<213> ORGANISM: Homo sapiens
<220> FEATURE:
<221> NAME/KEY: misc_feature
<222> LOCATION: 432
<223> OTHER INFORMATION: n = A,T,C or G

<400> SEQUENCE: 19
tctagcttca gtttctcctg cttcagttta aattgggaaa gagagagaaa aaatattcac    60
tcattatctg tttcctaaaa ttgtccttaa catccttcct cttactcctt tattacctgg   120
tcgggcttcc cctcttcagg cgaaatctgt cagtctatct gcattgcctt ttgatctcta   180
cttcagttac tacaacttca aagacaccat tgtcctcccc aaggtgaggc ccatgtagag   240
aaaggatcac ttccttgctg aaagagaggg tcaaggggcg acccacgtgg gccctccctg   300
aaacccaggc ccaggcctga gcctggacac ctccttcctt cctgagacca cagccagccc   360
ggtttctctg gggccaagag caaatgcttt gcttaagtgc tgaaatctca gcccactgac   420
cccttgcaga cnggagagga ggggaagccc agggaagctc aacttcccaa gtgtcctgag   480
tctctg                                                              486

<210> SEQ ID NO 20
<211> LENGTH: 484
<212> TYPE: DNA
<213> ORGANISM: Homo sapiens
<220> FEATURE:
<221> NAME/KEY: misc_feature
<222> LOCATION: 430
<223> OTHER INFORMATION: n = A,T,C or G

<400> SEQUENCE: 20
tagcttcagt ttctcctgct tcagtttaaa ttgggaaaga gagagaaaaa atattcactc    60
attatctgtt tcctaaaatt gtccttaaca tccttcctct tactccttta ttacctggtc   120
```

```
gggcttcccc tcttcaggcg aaatctgtca gtctatctgc attgccttt  gatctctact    180 tcagttacta caacttcaaa gacaccattg tcctccccaa ggtgaggccc atgtagagaa    240
aggatcactt ccttgctgaa agagagggtc aaggggcgac ccacgtgggc cctccctgaa    300
acccaggccc aggcctgagc ctggacacct ccttccttcc tgagaccaca gccagcccgg    360
tttctctggg gccaagagca aatgctttgc ttaagtgctg aaatctcagc ccactgaccc    420
cttgcagacn ggagaggagg ggaagcccag ggaagctcaa cttcccaagt gtcctgagtc    480
tctg                                                                484

<210> SEQ ID NO 21
<211> LENGTH: 485
<212> TYPE: DNA
<213> ORGANISM: Homo sapiens
<220> FEATURE:
<221> NAME/KEY: misc_feature
<222> LOCATION: 431
<223> OTHER INFORMATION: n = A,T,C or G

<400> SEQUENCE: 21
ctagcttcag tttctcctgc ttcagtttaa attgggaaag agagagaaaa aatattcact     60
yattatctgt ttcctaaaat tgtccttaac atccttcctc ttactccttt attacctggt    120
cgggcttccc ctcttcaggc gaaatctgtc agtctatctg cattgccttt tgatctctac    180
ttcagttact acaacttcaa agacaccatt gtcctcccca aggtgaggcc catgtagaga    240
aaggatcact ccttgctgaa gagagggt caaggggcga cccacgtggg ccctccctga    300
aacccaggcc caggcctgag cctggacacc tccttccttc ctgagaccac agccagcccg    360
gtttctctgg ggccaagagc aaatgctttg cttaagtgct gaaatctcag cccactgacc    420
ccttgcagac nggagaggag gggaagccca gggaagctca acttcccaag tgtcctgagt    480
ctctg                                                               485

<210> SEQ ID NO 22
<211> LENGTH: 488
<212> TYPE: DNA
<213> ORGANISM: Homo sapiens
<220> FEATURE:
<221> NAME/KEY: misc_feature
<222> LOCATION: 434
<223> OTHER INFORMATION: n = A,T,C or G

<400> SEQUENCE: 22
tgtctagctt cagtttctcc tgcttcagtt taaattggga agagagaga aaaatattc     60 acttattatc tgtttcctaa aattgtcctt aacatccttc ctcttactcc tttattacct    120
ggtcgggctt cccctcttca ggcgaaatct gtcagtctat ctgcattgcc ttttgatctc    180
tacttcagtt actacaactt caaagacacc attgtcctcc ccaaggtgag gcccatgtag    240
agaaaggatc acttccttgc tgaaagagag ggtcaagggg cgaccacgt gggccctccc    300 tgaaacccag gcccaggcct gagcctggac acctccttcc ttcctgagac acagccagc    360 ccggtttctc tggggccaag agcaaatgct ttgcttaagt gctgaaatct cagcccactg    420
accccttgca gacnggagag gaggggaagc ccagggaagc tcaacttccc aagtgtcctg    480
agtctctg                                                            488

<210> SEQ ID NO 23
<211> LENGTH: 488
<212> TYPE: DNA
<213> ORGANISM: Homo sapiens
```

<220> FEATURE:
<221> NAME/KEY: misc_feature
<222> LOCATION: 434
<223> OTHER INFORMATION: n = A,T,C or G

<400> SEQUENCE: 23

```
tgtctagctt cagtttctcc tgcttcagtt taaattggga agagagaga aaaatattc      60
acttattatc tgtttcctaa aattgtcctt aacatcctc ctcttactcc tttattacct    120
ggtcgggctt cccctcttca ggcgaaatct gtcagtctat ctgcattgcc ttttgatctc   180
tacttcagtt actacaactt caaagacacc attgtcctcc ccaaggtgag cccatgtag    240
agaaaggatc acttccttgc tgaaagagag ggtcaagggg cgacccacgt gggccctccc   300
tgaaacccag gcccaggcct gagcctggac acctccttcc ttcctgagac cacagccagc   360
ccggtttctc tggggccaag agcaaatgct tgcttaagt gctgaaatct cagcccactg    420
acccccttgca gacnggagag gaggggaagc ccagggaagc tcaacttccc aagtgtcctg   480
agtctctg                                                             488
```

<210> SEQ ID NO 24
<211> LENGTH: 497
<212> TYPE: DNA
<213> ORGANISM: Homo sapiens

<400> SEQUENCE: 24

```
tcactaggct tctggttgat gcctgtgaac tgaactctga caacagactt ctgaaataga    60
cccacaagag gcagttccat ttcatttgtg ccagaatgct ttaggatgta cagttatgga   120
ttgaaagttt acaggaaaaa aaattaggcc gttccttcaa agcaaatgtc ttcctggatt   180
attcaaaatg atgtatgttg aagcctttgt aaattgtcag atgctgtgca atgttatta    240
ttttaaacat tatgatgtgt gaaaactggt taatatttat aggtcacttt gttttactgt   300
cttaagttta tactcttata gacaacatgg ccgtgaactt tatgctgtaa ataatcagag    360
gggaataaac tgttgagtca aacagccat cttccttgtg accaaacatt taaaaatatt    420
ctggctgggc acagtggctc acgcctgtaa tcccagcact tgggaggcc gaggtgggca    480
gatcacctga ggttggg                                                   497
```

<210> SEQ ID NO 25
<211> LENGTH: 460
<212> TYPE: DNA
<213> ORGANISM: Homo sapiens

<400> SEQUENCE: 25

```
tgacaacaga cttctgaaat agacccacaa gaggcagttc catttcattt gtgccagaat    60
gctttaggat gtacagttat ggattgaaag tttacaggaa aaaaaattag gccgttcctt   120
caaagcaaat gtcttcctgg attattcaaa atgatgtatg ttgaagcctt tgtaaattgt   180
cagatgctgt gcaaatgtta ttattttaaa cattatgatg tgtgaaaact ggttaatatt   240
tataggtcac tttgttttac tgtcttaagt ttatactctt atagacaaca tggccgtgaa    300
ctttatgctg taaataatca gagggaata aactgttgag tcaaaacagc catcttcctt    360
gtgaccaaac atttaaaaat attctggctg gcacagtgg ctcacgcctg taatcccagc    420
actttgggag gccgaggtgg gcagatcacc tgaggttggg                          460
```

<210> SEQ ID NO 26
<211> LENGTH: 462
<212> TYPE: DNA

<213> ORGANISM: Homo sapiens

<400> SEQUENCE: 26

```
tctgacaaca gacttctgaa atagacccac aagaggcagt tccatttcat ttgtgccaga    60
atgctttagg atgtacagtt atggattgaa agtttacagg aaaaaaaatt aggccgttcc   120
ttcaaagcaa atgtcttcct ggattattca aaatgatgta tgttgaagcc tttgtaaatt   180
gtcagatgct gtgcaaatgt tattatttta acattatga tgtgtgaaaa ctggttaata   240
tttataggtc actttgtttt actgtcttaa gtttatactc ttatagacaa catggccgtg   300
aactttatgc tgtaaataat cagaggggaa taaactgttg agtcaaaaca gccatcttcc   360
ttgtgaccaa acatttaaaa atattctggc tgggcacagt ggctcacgcc tgtaatccca   420
gcactttggg aggccgaggt gggcagatca cctgaggttg gg                      462
```

<210> SEQ ID NO 27
<211> LENGTH: 459
<212> TYPE: DNA
<213> ORGANISM: Homo sapiens

<400> SEQUENCE: 27

```
gacaacagac ttctgaaata gacccacaag aggcagttcc atttcatttg tgccagaatg    60
ctttaggatg tacagttatg gattgaaagt ttacaggaaa aaaaattagg ccgttccttc   120
aaagcaaatg tcttcctgga ttattcaaaa tgatgtatgt tgaagccttt gtaaattgtc   180
agatgctgtg caaatgttat tattttaaac attatgatgt gaaaactg gttaatattt   240
ataggtcact ttgttttact gtcttaagtt tatactctta tagacaacat ggccgtgaac   300
tttatgctgt aaataatcag aggggaataa actgttgagt caaaacagcc atcttccttg   360
tgaccaaaca tttaaaaata ttctggctgg gcacagtggc tcacgcctgt aatcccagca   420
ctttgggagg ccgaggtggg cagatcacct gaggttggg                          459
```

<210> SEQ ID NO 28
<211> LENGTH: 467
<212> TYPE: DNA
<213> ORGANISM: Homo sapiens

<400> SEQUENCE: 28

```
tgaactctga acagacttt ctgaaataga cccacaagag gcagttccat ttcatttgtg    60
ccagaatgct ttaggatgta cagttatgga ttgaaagttt acaggaaaaa aaattaggcc   120
gttccttcaa agcaaatgtc ttcctggatt attcaaaatg atgtatgttg aagcctttgt   180
aaattgtcag atgctgtgca aatgttatta ttttaaacat tatgatgtgt gaaaactggt   240
taatatttat aggtcacttt gttttactgt cttaagttta tactcttata gacaacatgg   300
ccgtgaactt tatgctgtaa ataatcagag gggaataaac tgttgagtca aaacagccat   360
cttccttgtg accaaacatt taaaaatatt ctggctgggc acagtggctc acgcctgtaa   420
tcccagcact ttgggaggcc gaggtgggca gatcacctga ggttggg                 467
```

<210> SEQ ID NO 29
<211> LENGTH: 467
<212> TYPE: DNA
<213> ORGANISM: Homo sapiens

<400> SEQUENCE: 29

```
tgaactctga acagacttt ctgaaataga cccacaagag gcagttccat ttcatttgtg    60
ccagaatgct ttaggatgta cagttatgga ttgaaagttt acaggaaaaa aaattaggcc   120
```

| | |
|---|---|
| gttccttcaa agcaaatgtc ttcctggatt attcaaaatg atgtatgttg aagcctttgt | 180 |
| aaattgtcag atgctgtgca aatgttatta ttttaaacat tatgatgtgt gaaaactggt | 240 |
| taatatttat agrtcacttt gttttactgt cttaagttta tactcttata gacaacatgg | 300 |
| ccgtgaactt tatgctgtaa ataatcagag gggaataaac tgttgagtca aaacagccat | 360 |
| cttccttgtg accaaacatt taaaaatatt ctggctgggc acagtggctc acgcctgtaa | 420 |
| tcccagcact ttgggaggcc gaggtgggca gatcacctga ggttggg | 467 |

<210> SEQ ID NO 30
<211> LENGTH: 466
<212> TYPE: DNA
<213> ORGANISM: Homo sapiens

<400> SEQUENCE: 30

| | |
|---|---|
| gaactatgac aacagacttc tgaaatagac ccacaagagg cagttccatt tcatttgtgc | 60 |
| cagaatgctt taggatgtac agttatggat tgaaagttta caggaaaaaa aattaggccg | 120 |
| ttccttcaaa gcaatgtct tcctggatta ttcaaaatga tgtatgttga agcctttgta | 180 |
| aattgtcaga tgctgtgcaa atgttattat tttaaacatt atgatgtgtg aaaactggtt | 240 |
| aatatttata grtcactttg ttttactgtc ttaagtttat actcttatag acaacatggc | 300 |
| cgtgaacttt atgctgtaaa taatcagagg ggaataaact gttgagtcaa aacagccatc | 360 |
| ttccttgtga ccaaacattt aaaaatattc tggctgggca cagtggctca cgcctgtaat | 420 |
| cccagcactt tgggaggccg aggtgggcag atcacctgag gttggg | 466 |

<210> SEQ ID NO 31
<211> LENGTH: 466
<212> TYPE: DNA
<213> ORGANISM: Homo sapiens

<400> SEQUENCE: 31

| | |
|---|---|
| gaactctgac aacagacttc tgaaatagac ccacaagagg cagttccatt tcatttgtgc | 60 |
| cagaatgctt taggatgtac agttatggat tgaaagttta caggaaaaaa aattaggccg | 120 |
| ttccttcaaa gcaatgtct tcctggatta ttcaaaatga tgtatgttga agcctttgta | 180 |
| aattgtcaga tgctgtgcaa atgttattat tttaaacatt atgatgtgtg aaaactggtt | 240 |
| aatatttata grtcactttg ttttactgtc ttaagtttat actcttatag acaacatggc | 300 |
| cgtgaacttt atgctgtaaa taatcagagg ggaataaact gttgagtcaa aacagccatc | 360 |
| ttccttgtga ccaaacattt aaaaatattc tggctgggca cagtggctca cgcctgtaat | 420 |
| cccagcactt tgggaggccg aggtgggcag atcacctgag gttggg | 466 |

<210> SEQ ID NO 32
<211> LENGTH: 460
<212> TYPE: DNA
<213> ORGANISM: Homo sapiens

<400> SEQUENCE: 32

| | |
|---|---|
| tgacaacaga cttctgaaat agacccacaa gaggcagttc catttcattt gtgccagaat | 60 |
| gctttaggat gtacagttat ggattgaaag tttacaggaa aaaaattag gccgttcctt | 120 |
| caaagcaaat gtcttcctgg attattcaaa atgatgtatg ttgaagcctt tgtaaattgt | 180 |
| cagatgctgt gcaaatgtta ttattttaaa cattatgatg tgtgaaaact ggttaatatt | 240 |
| tatagrtcac tttgttttac tgtcttaagt ttatactctt atagacaaca tggccgtgaa | 300 |

-continued

| | |
|---|---|
| ctttatgctg taaataatca gaggggaata aactgttgag tcaaaacagc catcttcctt | 360 |
| gtgaccaaac atttaaaaat attctggctg ggcacagtgg ctcacgcctg taatcccagc | 420 |
| actttgggag gccgaggtgg gcagatcacc tgaggttggg | 460 |

<210> SEQ ID NO 33
<211> LENGTH: 467
<212> TYPE: DNA
<213> ORGANISM: Homo sapiens

<400> SEQUENCE: 33

| | |
|---|---|
| tgaactctga caacagactt ctgaaataga cccacaagag gcagttccat ttcatttgtg | 60 |
| ccagaatgct ttaggatgta cagttatgga ttgaaagttt acaggaaaaa aaattaggcc | 120 |
| gttccttcaa agcaaatgtc ttcctggatt attcaaaatg atgtatgttg aagcctttgt | 180 |
| aaattgtcag atgctgtgca atgttatta ttttaaacat tatgatgtgt gaaaactggt | 240 |
| taatatttat aggtcacttt gttttactgt cttaagttta tactcttata gacaacatgg | 300 |
| ccgtgaactt tatgctgtaa ataatcagag gggaataaac tgttgagtca aaacagccat | 360 |
| cttccttgtg accaaacatt taaaatatt ctggctgggc acagtggctc acgcctgtaa | 420 |
| tcccagcact tgggaggcc gaggtgggca gatcacctga ggttggg | 467 |

<210> SEQ ID NO 34
<211> LENGTH: 460
<212> TYPE: DNA
<213> ORGANISM: Homo sapiens

<400> SEQUENCE: 34

| | |
|---|---|
| tgacaacaga cttctgaaat agacccacaa gaggcagttc catttcattt gtgccagaat | 60 |
| gctttaggat gtacagttat ggattgaaag tttacaggaa aaaaaattag gccgttcctt | 120 |
| caaagcaaat gtcttcctgg attattcaaa atgatgtatg ttgaagcctt tgtaaattgt | 180 |
| cagatgctgt gcaaatgtta tattttaaa cattatgatg tgtgaaaact ggttaatatt | 240 |
| tatagatcac tttgttttac tgtcttaagt ttatactctt atagacaaca tggccgtgaa | 300 |
| ctttatgctg taaataatca gaggggaata aactgttgag tcaaaacagc catcttcctt | 360 |
| gtgaccaaac atttaaaaat attctggctg ggcacagtgg ctcacgcctg taatcccagc | 420 |
| actttgggag gccgaggtgg gcagatcacc tgaggttggg | 460 |

<210> SEQ ID NO 35
<211> LENGTH: 462
<212> TYPE: DNA
<213> ORGANISM: Homo sapiens

<400> SEQUENCE: 35

| | |
|---|---|
| tctgacaaca gacttctgaa atagacccac aagaggcagt tccatttcat ttgtgccaga | 60 |
| atgcttagg atgtacagtt atggattgaa agtttacagg aaaaaaaatt aggccgttcc | 120 |
| ttcaaagcaa atgtcttcct ggattattca aaatgatgta tgttgaagcc tttgtaaatt | 180 |
| gtcagatgct gtgcaaatgt tattatttta acattatga tgtgtgaaaa ctggttaata | 240 |
| tttatagatc actttgtttt actgtcttaa gtttatactc ttatagacaa catggccgtg | 300 |
| aactttatgc tgtaaataat cagagggaa taaactgttg agtcaaaaca gccatcttcc | 360 |
| ttgtgaccaa acatttaaaa atattctggc tgggcacagt ggctcacgcc tgtaatccca | 420 |
| gcactttggg aggccgaggt gggcagatca cctgaggttg gg | 462 |

<210> SEQ ID NO 36
<211> LENGTH: 463
<212> TYPE: DNA
<213> ORGANISM: Homo sapiens

<400> SEQUENCE: 36

```
ctctgacaac agacttctga aatagaccca caagaggcag ttccatttca tttgtgccag    60
aatgctttag gatgtacagt tatggattga aagtttacag gaaaaaaaat taggccgttc   120
cttcaaagca aatgtcttcc tggattattc aaaatgatgt atgttgaagc ctttgtaaat   180
tgtcagatgc tgtgcaaatg ttattatttt aaacattatg atgtgtgaaa actggttaat   240
atttatagrt cactttgttt tactgtctta agtttatact cttatagaca acatggccgt   300
gaactttatg ctgtaaataa tcagagggga ataaactgtt gagtcaaaac agccatcttc   360
cttgtgacca aacatttaaa aatattctgg ctgggcacag tggctcacgc ctgtaatccc   420
agcactttgg gaggccgagg tgggcagatc acctgaggtt ggg                    463
```

<210> SEQ ID NO 37
<211> LENGTH: 17
<212> TYPE: DNA
<213> ORGANISM: Homo sapiens

<400> SEQUENCE: 37

```
ggtggctggg ctcttct                                                   17
```

<210> SEQ ID NO 38
<211> LENGTH: 24
<212> TYPE: DNA
<213> ORGANISM: Homo sapiens

<400> SEQUENCE: 38

```
ctcgcttcct cagtacctat gatg                                           24
```

<210> SEQ ID NO 39
<211> LENGTH: 21
<212> TYPE: DNA
<213> ORGANISM: Homo sapiens

<400> SEQUENCE: 39

```
ctggctgagt gccagacatc t                                              21
```

<210> SEQ ID NO 40
<211> LENGTH: 17
<212> TYPE: DNA
<213> ORGANISM: Homo sapiens

<400> SEQUENCE: 40

```
ggcgggatgg agtggaa                                                   17
```

<210> SEQ ID NO 41
<211> LENGTH: 21
<212> TYPE: DNA
<213> ORGANISM: Homo sapiens

<400> SEQUENCE: 41

```
ccacctcaag ctctggtgat c                                              21
```

<210> SEQ ID NO 42
<211> LENGTH: 23
<212> TYPE: DNA
<213> ORGANISM: Homo sapiens

```
<400> SEQUENCE: 42
gttgactctt ttggccttttt cag                                          23

<210> SEQ ID NO 43
<211> LENGTH: 23
<212> TYPE: DNA
<213> ORGANISM: Homo sapiens

<400> SEQUENCE: 43
ccttaccaga cttccaggat ggt                                           23

<210> SEQ ID NO 44
<211> LENGTH: 25
<212> TYPE: DNA
<213> ORGANISM: Homo sapiens

<400> SEQUENCE: 44
tgtccaataa ctgcatcacc tacct                                         25

<210> SEQ ID NO 45
<211> LENGTH: 13
<212> TYPE: DNA
<213> ORGANISM: Homo  sapiens

<400> SEQUENCE: 45
catggctgga ccc                                                      13

<210> SEQ ID NO 46
<211> LENGTH: 13
<212> TYPE: DNA
<213> ORGANISM: Homo  sapiens

<400> SEQUENCE: 46
catggctgga tcc                                                      13

<210> SEQ ID NO 47
<211> LENGTH: 13
<212> TYPE: DNA
<213> ORGANISM: Homo  sapiens

<400> SEQUENCE: 47
tgctccggcg cca                                                      13

<210> SEQ ID NO 48
<211> LENGTH: 14
<212> TYPE: DNA
<213> ORGANISM: Homo  sapiens

<400> SEQUENCE: 48
ctgctctggc gcca                                                     14

<210> SEQ ID NO 49
<211> LENGTH: 16
<212> TYPE: DNA
<213> ORGANISM: Homo  sapiens

<400> SEQUENCE: 49
ctctgttgcc ccagaa                                                   16

<210> SEQ ID NO 50
<211> LENGTH: 15
<212> TYPE: DNA
<213> ORGANISM: Homo  sapiens
```

```
<400> SEQUENCE: 50
ctctgttgcg ccaga                                                    15

<210> SEQ ID NO 51
<211> LENGTH: 15
<212> TYPE: DNA
<213> ORGANISM: Homo sapiens

<400> SEQUENCE: 51
ctttcaaggg cctgc                                                    15

<210> SEQ ID NO 52
<211> LENGTH: 15
<212> TYPE: DNA
<213> ORGANISM: Homo sapiens

<400> SEQUENCE: 52
cctttcaagg ggcct                                                    15

<210> SEQ ID NO 53
<211> LENGTH: 16
<212> TYPE: DNA
<213> ORGANISM: Homo sapiens

<400> SEQUENCE: 53
aagactcgag tgtcct                                                   16

<210> SEQ ID NO 54
<211> LENGTH: 16
<212> TYPE: DNA
<213> ORGANISM: Homo sapiens

<400> SEQUENCE: 54
agactcaagt gtcctc                                                   16

<210> SEQ ID NO 55
<211> LENGTH: 533
<212> TYPE: DNA
<213> ORGANISM: Homo sapiens

<400> SEQUENCE: 55
ttcgtctcag tttgtttgtg agcaggctgt gagtttgggc cccagaggct gggtgacatg      60
tgttggcagc tcttcaaaaa tgagcccgtg cctgcctaag gctgaacttg ttttctggga     120
acaccatagg tcacctttat tctggcagag gagggagcat cagtgccctc caggatagac     180
ttttcccaag cctactttg ccattgactt cttcccaaga ttcaatccca ggatgtacaa      240
ggacagcccc tcctccatag tatgggactg gcctctgctg atcctcccag gcttccgtgt     300
gggtcagtgg ggcccatgga tgtgcttgtt aactgagtgc cttttggtgg agaggcccgg     360
cctctcacaa aagacccctt accactgctc tgatgaagag gagtacacag aacacataat     420
tcaggaagca gctttcccca tgtctcgact catccatcca ggccattccc cgtctctggt     480
tcctcccctc ctcctggact cctgcacacg ctccttcctc tgaggctgaa att           533

<210> SEQ ID NO 56
<211> LENGTH: 497
<212> TYPE: DNA
<213> ORGANISM: Homo sapiens

<400> SEQUENCE: 56
```

```
gggcccagca ggctgggtga catgtgttgg cagcctcttc aaaatgagcc ctgtcctgcc      60
taaggctgaa cttgttttct gggaacacca taggtcacct ttattctggc agaggaggga    120
gcatcagtgc cctccaggat agactttttcc caagcctact tttgccattg acttcttccc    180
aagattcaat cccaggatgt acaaggacag cccctcctcc atagtatggg actggcctct    240
gctgatcctc ccaggcttcc gtgtgggtca gtggggccca tggatgtgct tgttaactga    300
gtgccttttg gtggagaggc ccggcctctc acaaaagacc ccttaccact gctctgatga    360
agaggagtac acagaacaca taattcagga agcagctttc cccatgtctc gactcatcca    420
tccaggccat tccccgtctc tggttcctcc cctcctcctg gactcctgca cacgctcctt    480
cctctgaggc tgaaatt                                                   497
```

<210> SEQ ID NO 57
<211> LENGTH: 497
<212> TYPE: DNA
<213> ORGANISM: Homo sapiens

<400> SEQUENCE: 57

```
gggcccagca ggctgggtga catgtgttgg aagcctcttc aaaatgagcc ctgtcctgcc      60
taaggctgaa cttgttttct gggaacacca taggtcacct ttattctggc agaggaggga    120
gcatcagtgc cctccaggat agactttttcc caagcctact tttgccattg acttcttccc    180
aagattcaat cccaggatgt acaaggacag cccctcctcc atagtatggg actggcctct    240
gctgatcctc ccaggcttcc gtgtgggtca gtggggccca tggatgtgct tgttaactga    300
gtgccttttg gtggagaggc ccggcctctc acaaaagacc ccttaccact gctctgatga    360
agaggagtac acagaacaca taattcagga agcagctttc cccatgtctc gactcatcca    420
tccaggccat tccccgtctc tggttcctcc cctcctcctg gactcctgca cacgctcctt    480
cctctgaggc tgaaatt                                                   497
```

<210> SEQ ID NO 58
<211> LENGTH: 497
<212> TYPE: DNA
<213> ORGANISM: Homo sapiens

<400> SEQUENCE: 58

```
gggcccagca ggctgggtga catgtgttgg cagcctcttc aaaatgagcc ctgtcctgcc      60
taaggctgaa cttgttttct gggaacacca taggtcacct ttattctggc agaggaggga    120
gcatcagtgc cctccaggat agactttttcc caagcctact tttgccattg acttcttccc    180
aagattcaat cccaggatgt acaaggacag cccctcctcc atagtatggg actggcctct    240
gctgatcctc ccaggcttcc gtgtgggtca gtggggccca tggatgtgct tgttaactga    300
gtgccttttg gtggagaggc ccggcctctc acaaaagacc ccttaccact gctctgatga    360
agaggagtac acagaacaca taattcagga agcagctttc cccatgtctc gactcatcca    420
tccaggccat tccccgtctc tggttcctcc cctcctcctg gactcctgca cacgctcctt    480
cctctgaggg tgaaatt                                                   497
```

<210> SEQ ID NO 59
<211> LENGTH: 483
<212> TYPE: DNA
<213> ORGANISM: Homo sapiens

<400> SEQUENCE: 59

```
gggtgacatg tgttggcagc ctcttcaaaa tgagccctgt cctgcctaag gctgaacttg      60
```

```
ttttctggga acaccatagg tcacctttat tctggcagag agggagcat cagtgccctc    120 caggatagac ttttcccaag cctactttg ccattgactt cttcccaaga ttcaatccca    180
ggatgtacaa ggacagcccc tcctccatag tatgggactg gcctctgctg atcctcccag   240
gcttccgtgt gggtcagtgg ggcccatgga tgtgcttgtt aactgagtgc cttttggtgg    300
agaggcccgg cctctcacaa aagacccctt accactgctc tgatgaagag gagtacacag   360
aacacmtaat tcaggaagca gctttcccca tgtctcgact catccatcca ggccattccc   420
cgtctctggt tcctcccctc ctcctggact cctgcacacg ctccttcctc tgaggctgaa    480
att                                                                  483
```

<210> SEQ ID NO 60
<211> LENGTH: 500
<212> TYPE: DNA
<213> ORGANISM: Homo sapiens

<400> SEQUENCE: 60

```
tttgggcccc agaggctggg tgacatgtgt tggcagcctc ttcaaaatga gccctgtcct    60
gcctaaggct gaacttgttt ctgggaaca ccataggtca cctttattct ggcagaggag    120
ggagcatcag tgccctccag gatagacttt tcccaagcct acttttgcca ttgacttctt    180
cccaagattc aatcccagga tgtacaagga cagcccctcc tccatagtat gggactggcc    240
tctgctgatc ctcccaggct ccgtgtgggt cagtggggc catggatgt gcttgttaac     300 tgagtgcctt ttggtggaga ggcccggcct ctcacaaaag accccttmcc actgctctga    360
tgaagaggag tacacagaac acataattca ggaagcagct tccccatgt ctcgactcat    420 ccatccaggc cattccccgt ctctggttcc tccctcctc ctggactcct gcacacgctc    480
cttcctctga ggctgaaatt                                                500
```

<210> SEQ ID NO 61
<211> LENGTH: 499
<212> TYPE: DNA
<213> ORGANISM: Homo sapiens

<400> SEQUENCE: 61

```
ttgggcccca gaggctgggt gacatgtgtt ggcagcctct tcaaaatgag ccctgtcctg    60
cctaaggctg aacttgtttt ctgggaacac cataggtcac ctttattctg gcagaggagg    120
gagcatcagt gccctccagg atagactttt cccaagccta cttttgccat tgacttcttc    180
ccaagattca atcccaggat gtacaaggac agcccctcct ccatagtatg ggactggcct    240
ctgctgatcc tcccaggctt ccgtgtgggt cagtggggcc catggatgtg cttgttaact    300
gagtgccttt tggtggagag gcccggcctc tcacaaaaga ccccttmcca ctgctctgat    360
gaagaggagt acacagaaca cataattcag gaagcagctt tccccatgtc tcgactcatc    420
catccaggcc attccccgtc tctggttcct ccctcctcc tggactcctg cacacgctcc    480
ttcctctgag gctgaaatt                                                 499
```

<210> SEQ ID NO 62
<211> LENGTH: 498
<212> TYPE: DNA
<213> ORGANISM: Homo sapiens

<400> SEQUENCE: 62

```
tgggcccag aggctgggtg acatgtgttg gcagcctctt caaaatgagc cctgtcctgc    60
```

```
ctaaggctga acttgttttc tgggaacacc ataggtcacc tttattctgg cagaggaggg      120
agcatcagtg ccctccagga tagacttttc ccaagcctac ttttgccatt gacttcttcc      180
caagattcaa tcccaggatg tacaaggaca gcccctcctc catagtatgg gactgggctc      240
tgctgatcct cccaggcttc cgtgtgggtc agtggggccc atggatgtgc ttgttaactg      300
agtgcctttt ggtggagagg cccggcctct cacaaaagac cccttmccac tgctctgatg      360
aagaggagta cacagaacac ataattcagg aagcagcttt ccccatgtct cgactcatcc      420
atccaggcca ttccccgtct ctggttcctc ccctcctcct ggactcctgc acacgctcct      480
tcctctgagg ctgaaatt                                                    498

<210> SEQ ID NO 63
<211> LENGTH: 498
<212> TYPE: DNA
<213> ORGANISM: Homo sapiens

<400> SEQUENCE: 63
tgggccccag aggctgggtg acatgtgttg gcagcctctt caaaatgagc cctgtcctgc       60
ctaaggctga acttgttttc tgggaacacc ataggtcacc tttattctgg cagaggaggg      120
agcatcagtg ccctccagga tagacttttc ccaagcctac ttttgccatt gacttcttcc      180
caagattcaa tcccaggatg tacaaggaca gcccctcctc catagtatgg gactggcctc      240
tgctgatcct cccaggcttc cgtgtgggtc agtggggccc atggatgtgc ttgttaactg      300
agtgcctttt ggtggagagg cccggcctct cacaaaagac cccttmccac tgctctgatg      360
aagaggagta cacagaacac ataattcagg aagcagcttt ccccatgtct cgactcatcc      420
atccaggcca ttccccgtct ctggttcctc ccctcctcct ggactcctgc acacgctcct      480
tcctctgagg ctgaaatt                                                    498

<210> SEQ ID NO 64
<211> LENGTH: 498
<212> TYPE: DNA
<213> ORGANISM: Homo sapiens

<400> SEQUENCE: 64
tgggccccag aggctgggtg acatgtgttg gcagcctctt caaaatgagc cctgtcctgc       60
ctaaggctga acttgttttc tgggaacacc ataggtcacc tttattctgg cagaggaggg      120
agcatcagtg ccctccagga tagacttttc ccaagcctac ttttgccatt gacttcttcc      180
caagattcaa tcccaggatg tacaaggaca gcccctcctc catagtatgg gactggcctc      240
tgctgatcct cccaggcttc cgtgtgggtc agtggggccc atggatgtgc ttgttaactg      300
agtgcctttt ggtggagagg cccggcctct cacaaaagac cccttaccac tgctctgatg      360
aagaggagta cacagaacac ataattcagg aagcagcttt ccccatgtct cgactcatcc      420
atccaggcca ttccccgtct ctggttcctc ccctcctcct ggactcctgc acacgctcct      480
tcctctgagg ctgaaatt                                                    498

<210> SEQ ID NO 65
<211> LENGTH: 503
<212> TYPE: DNA
<213> ORGANISM: Homo sapiens

<400> SEQUENCE: 65
gagtttgggc cccagaggct gggtgacatg tgttggcagc ctcttcaaaa tgagccctgt       60
cctgcctaag gctgaacttg ttttctggga acaccatagg tcacctttat tctggcagag      120
```

```
gagggagcat cagtgccctc caggatagac ttttcccaag cctactttg ccattgactt    180 cttcccaaga ttcaatccca ggatgtacaa ggacagcccc tcctccatag tatgggactg    240
gcctctgctg atcctcccag gcttccgtgt gggtcagtgg ggcccatgga tgtgcttgtt    300
aactgagtgc cttttggtgg agaggcccgg cctctcacaa aagacccctt cccactgctc    360
tgatgaagag gagtacacag aacacataat tcaggaagca gctttcccca tgtctcgact    420
catccatcca ggccattccc cgtctctggt tcctcccctc ctcctggact cctgcacacg    480
ctccttcctc tgaggctgaa att                                            503

<210> SEQ ID NO 66
<211> LENGTH: 453
<212> TYPE: DNA
<213> ORGANISM: Homo sapiens

<400> SEQUENCE: 66
tgagccctgt cctgcctaag gctgaacttg ttttctggga acaccatagg tcacctttat     60
tctggcagag gagggagcat cagtgccctc caggatagac ttttcccaag cctactttg    120 ccattgactt cttcccaaga ttcaatccca ggatgtacaa ggacagcccc tcctccatag    180
tatgggactg gcctctgctg atcctcccag gcttccgtgt gggtcagtgg ggcccatgga    240
tgtgcttgtt aactgagtgc cttttggtgg agaggcccsg cctctcacaa aagacccctt    300
cccactgctc tgatgaagag gagtacacag aacacataat tcaggaagca gctttcccca    360
tgtctcgact catccatcca ggccattccc cgtctctggt tcctcccctc ctcctggact    420
cctgcacacg ctccttcctc tgaggctgaa att                                  453

<210> SEQ ID NO 67
<211> LENGTH: 500
<212> TYPE: DNA
<213> ORGANISM: Homo sapiens

<400> SEQUENCE: 67
tttgggcccc agaggctggg tgacatgtgt tggcagcctc ttcaaaatga gccctgtcct     60
gcctaaggct gaacttgttt tctgggaaca ccataggtca cctttattct ggcagaggag    120
ggagcatcag tgccctccag gatagacttt tcccaagcct acttttgcca ttgacttctt    180
cccaagattc aatcccagga tgtacaagga cagcccctcc tccatagtat gggactggcc    240
tctgctgatc ctcccaggct tccgtgtggg tcagtgggc ccatggatgt gcttgttaac    300
tgagtgcctt ttggtggaga ggcccggcct ctcacaaaag acccttmcc actgctctga    360 tgaagaggag tacacagaac acataattca ggaagcagct ttccccatgt ctcgactcat    420
ccatccaggc cattccccgt ctctggttcc tcccctcctc ctggactcct gcacacgctc    480
cttcctctga gggtgaaatt                                                500
```